United States Patent
Coakley et al.

(10) Patent No.: US 11,464,499 B2
(45) Date of Patent: Oct. 11, 2022

(54) DEVICE FOR ANATOMICAL SENSING SYSTEM-GUIDED ENDORECTAL PROSTATE BIOPSY

(71) Applicant: Oregon Health & Science University, Portland, OR (US)

(72) Inventors: Fergus Coakley, Portland, OR (US); Stevan Wittenbrock, Portland, OR (US); Forrest Seitz, Beaverton, OR (US); Christopher J. Jensen, Beaverton, OR (US); Daniel R. Baker, Seattle, WA (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 898 days.

(21) Appl. No.: 16/329,061

(22) PCT Filed: Sep. 1, 2017

(86) PCT No.: PCT/US2017/049954
§ 371 (c)(1),
(2) Date: Feb. 27, 2019

(87) PCT Pub. No.: WO2018/045342
PCT Pub. Date: Mar. 8, 2018

(65) Prior Publication Data
US 2019/0192125 A1  Jun. 27, 2019

Related U.S. Application Data

(60) Provisional application No. 62/382,631, filed on Sep. 1, 2016.

(51) Int. Cl.
A61B 10/02 (2006.01)
A61B 5/00 (2006.01)
(Continued)

(52) U.S. Cl.
CPC .......... *A61B 10/0241* (2013.01); *A61B 6/032* (2013.01); *A61B 5/4381* (2013.01); *A61B 8/0841* (2013.01); *A61B 34/20* (2016.02)

(58) Field of Classification Search
CPC ... A61B 10/0241; A61B 5/4381; A61B 90/11; A61B 2017/00274
See application file for complete search history.

(56) References Cited

U.S. PATENT DOCUMENTS 6,464,691 B1  10/2002 Castaneda et al.
6,470,204 B1  10/2002 Uzgiris et al.
(Continued)

FOREIGN PATENT DOCUMENTS

JP  2008170006 A  7/2008
JP  2016505314 A  2/2016

*Primary Examiner* — Thaddeus B Cox
(74) *Attorney, Agent, or Firm* — Schwabe, Williamson & Wyatt, P.C.

(57) ABSTRACT

An anatomical sensing system-guided prostate procedure device that includes a housing having a proximal end and a distal end. The housing may be divided into a distal housing section, a mid housing section, and a proximal housing section, wherein the distal housing section is configured for insertion into the anus and retention in the rectum of a subject. The device further includes an instrument convergence point disposed between the proximal end and the distal end, the convergence point configured to allow an instrument pass though the instrument convergence point at a variable angle; and an instrument angle orienting system at the proximal end of the housing, the angle orienting system directing an orientation of the variable angle about the convergence point. Methods of the using an anatomical sensing system-guided prostate procedure device and system including the same.

21 Claims, 31 Drawing Sheets

(51) Int. Cl.
*A61B 6/03* (2006.01)
*A61B 34/20* (2016.01)
*A61B 8/08* (2006.01)

(56) References Cited

U.S. PATENT DOCUMENTS

| | | | |
|---|---|---|---|
| 8,123,697 B2 | 2/2012 | Daum et al. | |
| 2002/0045816 A1* | 4/2002 | Atalar | G01R 33/285 |
| | | | 324/318 |
| 2009/0247859 A1* | 10/2009 | Daum | A61B 90/10 |
| | | | 600/564 |
| 2010/0056900 A1* | 3/2010 | Whitcomb | A61B 34/30 |
| | | | 600/414 |
| 2014/0275978 A1 | 9/2014 | Fujimoto et al. | |
| 2015/0130467 A1 | 5/2015 | Biber et al. | |
| 2015/0265354 A1* | 9/2015 | Stoianovici | A61B 10/0241 |
| | | | 600/417 |
| 2015/0366544 A1* | 12/2015 | Yap | A61B 17/3403 |
| | | | 600/464 |

\* cited by examiner

DEVICE FOR ANATOMICAL SENSING SYSTEM-GUIDED ENDORECTAL PROSTATE BIOPSY

CROSS-REFERENCE

This application is a national phase entry under 35 U.S.C. § 371 of International Application No. PCT/US2017/049954, filed Sep. 1, 2017, which was published in English and designated, among the various States, the United States of America, and which claims the priority benefit of the earlier filing date of U.S. Provisional Application No. 62/382,631, filed Sep. 1, 2016, which is hereby incorporated herein by reference in its entirety.

STATEMENT OF GOVERNMENT INTEREST

This invention was made with government support under TR000128 awarded by the National Institutes of Health. The government has certain rights in the invention.

TECHNICAL FIELD

The present disclosure relates to the field of tissue biopsy. More specifically, to devices, systems, and methods for anatomical sensing system-targeted biopsy of prostate tissue.

BACKGROUND

Prostate cancer is a major socioeconomic problem. Approximately one million men undergo prostate biopsy every year in the United States (Loeb S et al, *J Urol* 186, 1830-1834 (2011)), typically after an abnormal serum prostatic specific antigen (PSA) level or digital rectal examination, and about 20% of these men have a positive result for cancer. Overall, the lifetime risk of prostate cancer diagnosis for an American man is about 1 in 6, and roughly 12% of those diagnosed will die of the disease. The current standard of care for prostate cancer diagnosis is systematic transrectal ultrasound guided biopsy, during which a urologist uses an ultrasound probe placed in the rectum to localize the prostate (but usually not the tumor) and obtains 12 or more needle core biopsies from standard locations in the gland. Prostate cancer is the only solid organ malignancy that is diagnosed by such random systematic biopsies. By way of contrast, it is inconceivable that breast cancer would be diagnosed by placing twelve needles at standard locations in the breast, yet this has been the longstanding "state-of-the-art" for prostate cancer. This standard approach is associated with disturbingly high rates of false negative diagnosis (missed cancer, 15-46%), overdiagnosis (detection of indolent Gleason 6 cancer of questionable clinical significance, 45%) and underdiagnosis (under grading of the cancer when compared to the final surgical pathology, 38%) (Dominguez-Escrig J L et al, *Prostate Cancer* 386207 (2011); Kvåle R et al, *BJU International* 103, 1647-54 (2009); Siddiqui M M et al, *Eur Urol* 64, 713-719 (2013)). Freehand systematic biopsy is also associated with unintended geometric error and clustering of needle positions, and reduced cancer detection when compared to templated systematic biopsy (Itatani R et al, *Eur J Radiol* 83, 1740-1745 (2014) and Han M et al, *J Urol;* 188: 2404-2409 (2012)).

In about 60% of patients with suspected prostate cancer, multiparametric prostate MRI can accurately demonstrate likely sites of disease for targeted biopsy (Moore C M et al, *Eur Urol* 63, 125-140 (2013)). Prostate MRI is best performed with a surface coil in the rectum, since the resulting improved signal-to-noise ratio significantly improves tumor detection and staging (Turkbey B et al, *J Magn Reson imaging* 39, 1443-1448 (2014) and Futterer J J et al, *Eur Radiol* 17, 1055-1065 (2007)). MRI-targeted biopsy has been shown to reduce the rates of false negative diagnosis, overdiagnosis, and underdiagnosis (Siddiqui M M et al, 2013 supra; Van de Ven W J M et al, *Nature Reviews Urology* 10, 559-556 (2013); Klein E A, *Nat Rev Clin Oncol* 12, 253-254 (2015); Nassiri N et al, *Urology* 86, 432-438 (2015); Mendhiratta N et al, *J Urol* 194, 1601-1606 (2015); Hoeks C M et al, *European Urology* 62, 902-909 (2012)). Improved tumor characterization and treatment stratification resulting from targeted biopsy can offset the initial costs associated with MRI over a 10-year horizon (de Rooij M et al, *European Urology* 66, 430-436 (2014)). However, cost, access, and scheduling concerns remain as barriers to wider adoption of MRI-targeted biopsy.

MRI-targeted biopsy can be performed using direct ("in bore") or fusion approaches, but each has limitations. A major limitation of both approaches, for example, is that they require two separate procedures—a diagnostic MRI followed by separate MRI-targeted biopsy—making the diagnostic pathway time-consuming and costly. Additional limitations of direct anatomical sensing system-guided biopsy are that systematic cores cannot be obtained during the procedure, and the quality of the biopsy images is reduced because an endorectal coil is not used. Limitations of fusion biopsy are that the needle is not seen traversing the target on the same modality (violating a basic principal of image-guided biopsy), and that intraprocedural deformation of the prostate may result in significant registration error with potential mistargeting during biopsy. Another common limitation is that both approaches require vendor-specific software. All of these factors point to a need for new systems and methods to advance the state of the art and improve diagnostic prostate biopsy procedures.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

BRIEF SUMMARY OF THE DISCLOSURE

Figure 1:
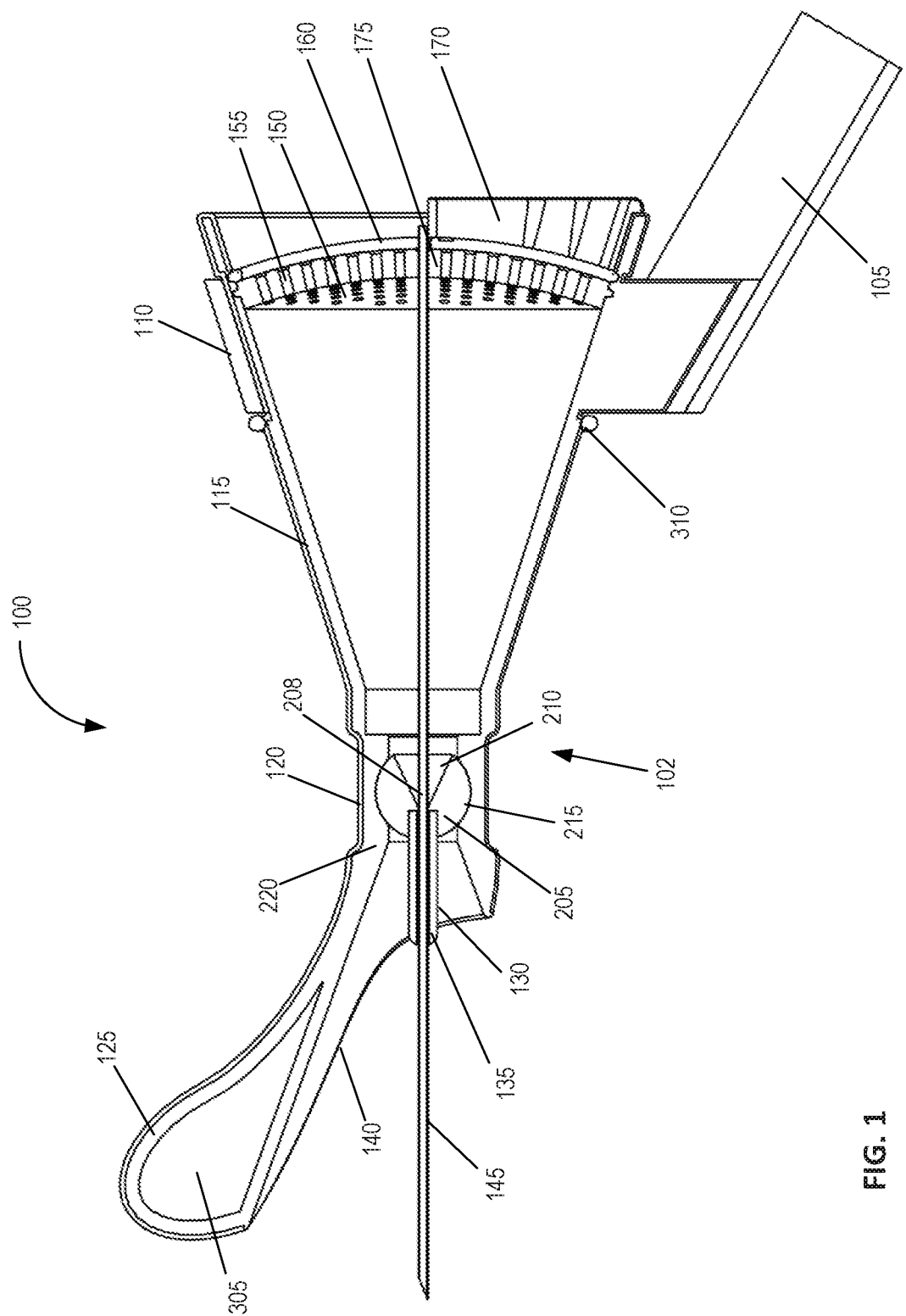
FIG. 1 is a cross sectional side view of an anatomical sensing system-guided prostate procedure device having a fixed curved array instrument angle orienting system, in accordance with various embodiments.

Provided herein is a medical device comprising a housing having a distal housing section, a proximal housing section, and an instrument convergence point wherein: the distal housing section is configured for insertion into the anus and retention in the rectum of a human; and the proximal housing section contains an angle orienting system; such that a medical instrument may pass between the angle orienting system and the convergence point for operation at variable angles.

Also provided herein is a medical device comprising a housing having a distal housing section, a proximal housing section, and a mid housing section wherein: the distal housing section is configured for insertion into the anus and retention in the rectum of a human; the proximal housing section contains an angle orienting system; and the mid housing section contains a convergence point; such that a medical instrument may pass between the angle orienting system and the convergence point for operation at variable angles.

In some embodiments, the medical devices comprise a prostate biopsy device in which the medical instrument is a biopsy needle.

In additional embodiments, the medical devices above further comprises an anatomical sensing system. Examples of anatomical sensing systems include, but are not limited to magnetic resonance sensing systems, active or passive electromagnetic sensing systems including, but not limited to, Computed Tomography (CT) anatomical sensing systems, ultrasound anatomical sensing systems, and laser anatomical sensing systems.

DETAILED DESCRIPTION OF DISCLOSED EMBODIMENTS

In the following detailed description, reference is made to the accompanying drawings, which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.). The modifier "about" used in connection with a quantity is inclusive of the stated value and has the meaning dictated by the context (e.g., includes the degree of error associated with measurement of the particular quantity). In the context of this disclosure, the term "subject" refers to an animal, such as a mammal, that has been or will be the object of treatment, observation or experiment. The devices, systems and methods described herein may be useful in both human therapy and veterinary applications. In some embodiments, the subject is a mammal; in some embodiments, the subject is human.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Prior to this disclosure there were two emerging options for MRI-targeted biopsy: fusion and in-bore approaches. Both entail a two-step process consisting of a diagnostic MRI procedure followed by a separate biopsy procedure. Both approaches also have significant limitations. In fusion biopsy, targets are identified on the MRI images and then "painted" onto a real-time transrectal ultrasound image so that the operator may direct needles at the target under ultrasound guidance. Fusion requires accurate co-registration of the MRI images onto the ultrasound image; any distortion of the prostate due to motion of the probe can cause misregistration between the MRI and ultrasound images and result in cancer being missed during targeting. In-bore biopsy requires slow and repeated adjustments of a single channel introducer until the channel is correctly pointing toward the target. Biopsy of more than one target requires repeating the adjustment process, thereby substantially increasing the duration of the procedure.

Disclosed herein is a novel device, system, and methods of using the same that reduces a prostate related procedure, such as a prostate biopsy, to a single procedure. In certain exemplary embodiments, the disclosed device allows for the combination of diagnostic prostate MRI with MRI-targeted biopsy. In embodiments, the disclosed device, system, and methods address the need for an accurate and cost-effective prostate biopsy procedure with the capacity to effectively target and obtain core samples using the least invasive method possible. As the number of cores obtained during systematic biopsy has increased and as the use of repeated biopsy to monitor patients on active surveillance has grown, multiple and serial biopsies are increasingly recognized to cause serious complications, including sepsis, impaired urination, and erectile dysfunction (see Loeb S et al, 2011 supra; Fujita K et al, *J Urol* 182, 2664-2669 (2009); Klein T et al, *J Urol* 184, 1447-1452 (2010)). Using a targeted, rather than a systematic, collection-based approach minimizes the risk of infection and allows for an optimal course of treatment. Furthermore, systematic biopsy is painful, with 25% of patients describing moderate to severe pain and 19% reporting they would refuse to undergo a repeat procedure. In contrast to the aforementioned fusion and in-bore approaches, the disclosed device, system, and method offers not only the advantages of targeting using high quality, anatomical sensing system data, such as MRI data, but also rapid acquisition of tissue from the highest value targets in the prostate. While particular attention has been given herein to anatomical sensing systems directed to Magnetic Resonance, the devices, systems, and methods disclosed herein can be used in conjunction with other imaging techniques using active or passive electromagnetic sensing systems, such as but not limited to, Computed Tomography (CT) anatomical sensing systems, Ultrasound anatomical sensing systems, and laser anatomical sensing systems.

Aspects of the current disclosure are related to a device for use in an anatomical sensing system-guided prostate procedure. Thus, disclosed is a device for anatomical sensing system-guided prostate procedures, such as, but not limited to, prostate biopsies. The device includes a housing having a proximal end and a distal end, the distal end being closer to the subject when in use and the proximal end being closer to the user, such as a medical professional, during insertion and/or use. In embodiments, the housing can be divided into a proximal end housing section, a mid housing section, and a distal end housing section for ease of description. The distal end housing section of the device is configured for insertion into the anus and retention in the rectum of a male subject, such as a human male subject. When inserted into the rectum of a male subject the distal end housing section of the device is retained in close proximity to the prostate gland (see, for example, FIG. 17). Retained in such a position, the device can be used to guide an instrument, such as a biopsy needle or other medical instrument, to specified sections or areas of the prostate, for example as specified and/or selected using data from an anatomical imaging system, such as images of the prostate obtained by, or from, an anatomical sensing system, for example from MRI images of the prostate. The device for anatomical sensing system-guided prostate procedures includes an instrument convergence point disposed between the proximal end and the distal end. The instrument convergence point is defined by an intersection of a proximal cone and a distal cone that together define the range of motion of an instrument both proximal and distal to the convergence point. The convergence point is configured to allow an instrument to pass through the instrument convergence point at a variable angle (for example the angle of an instrument having a shaft passing through the convergence point can be varied and/or selected). The device for anatomical sensing system-guided prostate procedures further includes an instrument angle orienting system at the proximal end of the housing, the angle orienting system directing an orientation of a variable angle with in the intersecting cones in three-dimensions about the convergence point (for example left/right, up/down, in/out).

The proximal housing section, the mid housing section, and the distal end housing section can be made of a single piece, for example a single piece of rigid plastic that is compatible with an anatomical sensing system, such as, but not limited to an MRI system. In some embodiments, the proximal housing section, the mid housing section, and the distal end housing section are made from multiple pieces that are fit together. In certain embodiments, the housing is substantially made of a rigid material, while in other embodiments, portions, such as certain portions of the distal housing section are made from less rigid materials, such that portions of the distal housing section can more easily conform to the anatomy of a subject and limit discomfort. Of note, in embodiments, while portions of the exterior of the device can be made from less rigid or flexible materials, the convergence point, the rigid parts of the distal housing section and the instrument angle orienting system are held in a fixed geometry relative to each other while the device is in use. Techniques of fabrication of such components is known in the art.

In embodiments, the distal end housing section includes a cut out that allows an instrument, such as a biopsy needle, to pass through the device, for example at various angles relative to the longitudinal axis of the device for example the axis of the mid housing section and the proximal housing section. In some examples, this cut out matches the cone of variability of the instrument angle, for example the distal cone described above. In some embodiments, the inferior aspect (toward the centerline (or longitudinal axis)) of the distal housing section includes the instrument access cutout from which an instrument, or other features of the device, can be deployed.

In embodiments, the distal housing section is angled superiorly away from the centerline (or longitudinal axis) of the proximal housing section and mid housing section, which are substantially aligned. The angle is configured to match the anatomy or at least approximate the anatomical features of an average male subject, for example the rectum of the average male subject. In embodiments, this angle may be between about 10 and about 45 degrees, such as about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 degrees, any fractions thereof, and any subset and ranges thereof. In other embodiments, this angle may be between about 10 degrees and about 60 degrees, such as the individual angles just mentioned, as well as those of 46, 47, 48, 49, 50, 51, 52, 53, 54, 55, 56, 57, 58, 59, and 60 degrees, as well as any fractions, subsets, and ranges thereof. In certain embodiments, this angle is adjustable.

Figure 4:
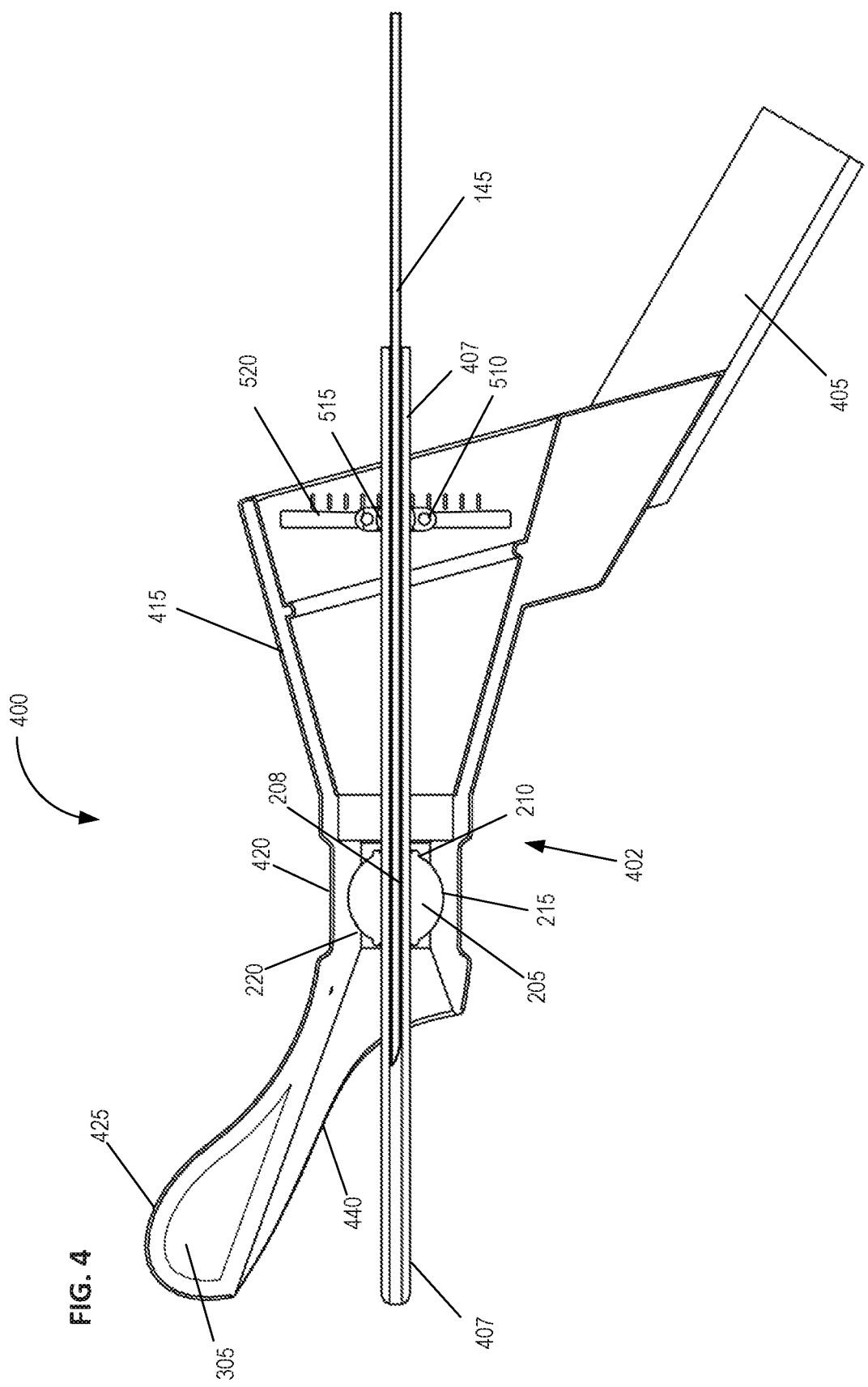
FIG. 4 is a cross sectional side view of an anatomical sensing system-guided prostate procedure device having a Cartesian coordinate instrument angle orienting system, in accordance with various embodiments.
Figure 7:
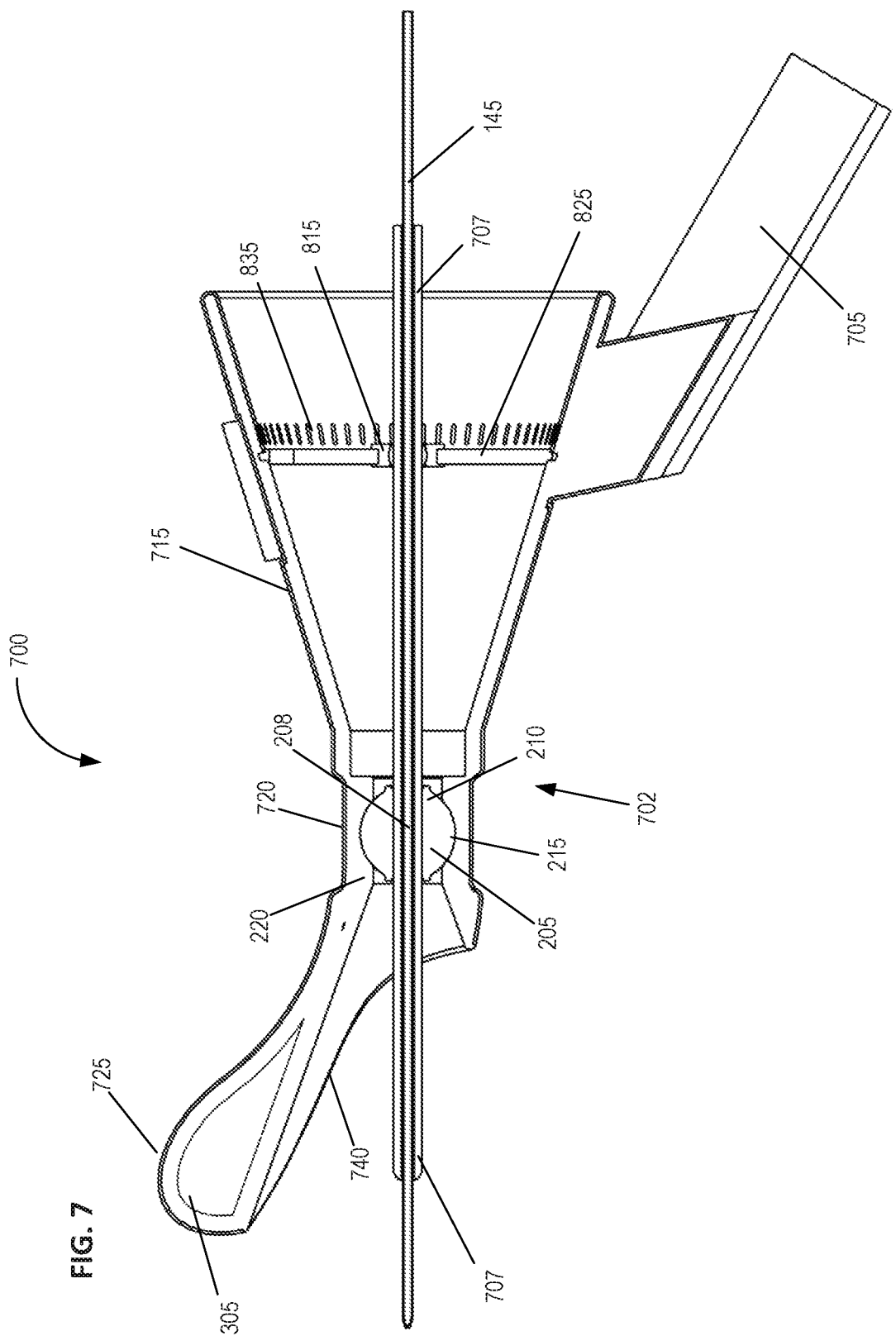
FIG. 7 is a cross sectional side view of an anatomical sensing system-guided prostate procedure device having a cylindrical coordinate instrument angle orienting system, in accordance with various embodiments.

In some embodiments, the distal housing, for example as seen as 125 in FIG. 1, 425 in FIG. 4, and 725 in FIG. 7, is manufactured to conform to the J-shape of the human rectum. In further embodiments, the distal surfaces of the distal housing section are rounded for ease of insertion and protection of anal and rectal tissues. In certain embodiments, distal housing section is sized to fit within the rectum of a subject. In certain embodiments, the distal end is substantially cylindrical and/or ovoid. In certain embodiments the distal housing section is about 0.5 inches to about 1.5 inches in width and/or radius. In certain embodiments, the distal housing includes a subhousing or compartment that protrudes from the main part of the distal housing section, for example, to house an imaging coil, such as a MRI coil.

In embodiments, the distal housing section includes an internal compartment, for example to house components of an anatomical sensing system, such as an MRI coil. Placement of components of an anatomical sensing system, such as an MRI coil, in the compartment, would improve imaging in the vicinity of the component and hence in the region of the prostate. The design of exemplary imaging coils, such as MRI imaging coils is provided below. When the distal end of the device includes an imaging coil (as disclosed below) the proximity of this coil to the prostate increases the quality, such as the signal-to-noise ratio, of the imaging data obtained. This allows for more precision in procedures using the disclosed device than other devices.

In embodiments, the device includes an instrument convergence point disposed between the proximal end and the distal end. The convergence point is configured to allow an instrument to pass though this point at a variable angle, for example a selectable angle. In other words, regardless of the angle at which the instrument is introduced into, or through the device, the instrument passes through the convergence point. This angle conforms to the angle of the intersecting cones as described above. In certain embodiments, the convergence point is configured to allow the instrument to move at an angle of between about 0 degrees and about 25 degrees in any direction, i.e. an about 50 degree cone from the convergence point, which can alternatively be thought of as yaw and pitch of the instrument. In certain embodiments, the instrument convergence point is contained within a mechanism configured to direct the instrument to three-dimensional locations distally, for example the distal end of the instrument. In certain embodiments, the instrument convergence point is located at the center of an aperture through which an instrument may pass. In certain embodiments, the instrument convergence point is located within a channel through which an instrument may pass. In certain embodiments, mathematical relationship between target tissue selected using data from the anatomical sensing system and the instrument convergence point are utilized for presenting the user with relative, or absolute, increments of movement on the proximal side plus insertion depth such that the target is intercepted. In certain embodiments, the instrument convergence point is imaged such that the relationship between the target and the convergence point is measured by the user interacting with the anatomical sensing system to determine where to move, the device and/or the instrument relatively or absolutely, so that the information derived can be easily inputted into the proximal housing section and instrument such that the instrument will intercept the intended target. Such imaging and/or data collection can be performed at any point in the procedure, for example during or after insertion, or even before insertion. In specific embodiments, the mid housing section of the anatomical sensing system-guided prostate procedure device includes a recessed waist within which the convergence point is located. In certain embodiments, the convergence point is translatable along an axis running from the proximal end of the device and the distal end of the device. In certain embodiments, the mid housing section is recessed and configured to be retained in the anus of a subject, for example such that the anal orifice collapses around the recessed waist and helps to hold and/or retain the device in place. In certain embodiments, the mid housing section is about 0.25 inches to about 1.0 inches in length. In certain embodiments, the mid housing section has a diameter of about 0.5 inches to about 1.0 inches.

In certain embodiments, the anatomical sensing system-guided prostate procedure device includes a spherical targeting ball rotationally constrained within the housing, such as within the mid housing section, and centered about the instrument convergence point. In certain embodiments, the spherical targeting ball has a proximal side and a distal side, the proximal side oriented to the proximal end of the device and the distal side oriented toward the distal end of the device. In embodiments, the spherical targeting ball is configured so that an instrument, such as a biopsy needle, can pass through the center of the spherical targeting ball and therefore through the convergence point. Thus, rotation of the spherical targeting ball about the convergence point allows the instrument to rotate about the convergence point. In certain embodiments, the convergence point includes an anatomical sensing system visible marker that can be used to indicate the position of the convergence point within image obtained with an anatomical sensing system. In some embodiments, the inner surface of the recessed waist within the mid housing section has a spherical bearing surface, against which the spherical targeting ball may rotate. In embodiments, the spherical bearing surface may include an anatomical sensing system detectable marker, for example it may contain a contrast agent compartment, for example for water/hydrogel or other material, to provide image contrast during MRI imaging. In certain embodiments, the spherical targeting ball may include an anatomical sensing system detectable marker it itself, or may be made from an anatomical sensing system detectable material. Such materials are known to those of skill the art. These features can be used as fiducial markers during system registration and tissue targeting, for example prostate targeting. For example, using software, such as imaging software, the position of the anatomical sensing system detectable marker feature of the device can be used to define the location of the device in multiple dimensions, such as three-dimensions with respect to one or more of the patient and the sensing system in which the device is being used.

In embodiments, the spherical targeting ball includes a conical cutout on the proximal side that is configured to receive an instrument passing therethrough. In embodiments, the spherical targeting ball includes a conical cut out on the proximal side, for example configured to receive a biopsy needle at an angle relative to the longitudinal axis of the device.

One of the features unique to the device is an instrument angle orienting system located at the proximal end of the housing. The angle orienting system directs orientation of the angle of the instrument in about the convergence point, for example as it passes through the convergence point the angle that the instrument makes relative to the long central axis of the device (for example the axis of the mid housing section and the proximal housing section) is dictated by the instrument angle orienting system. This instrument angle orienting system is located on the proximal end of the proximal housing section. The instrument angle orienting system is configured to retain an instrument, such as biopsy needle, at a specific angle, such as a pair of horizontal and vertically oriented angles relative to the horizontal and vertical planes of the device. By retaining the instrument at a specific angle relative to the device, which is itself is retained in a specific orientation relative to the subject, data obtained with a sensing system, such as images of the subject, for example MRI images, the instrument angle orienting system can be used to guide the placement of the instrument. By way of example, the distal end of the device is inserted into the patient's rectum such that the distal end housing section cut out is in proximity to the prostate. The proximal end of the device is coupled to a stationary clamp-stand, for example using a clamp handle coupled to the proximal housing section, to prevent movement of the device and, generally, the subject. For example, a DynaTRIM baseplate that is affixed to an MR imaging table can be attached to a DynaTRIM clamp-stand and used to maintain the position of the device. In this configuration, the instrument angle orienting system and convergence point are fixed relative to the prostate and an instrument, such as a biopsy needle, can be variably oriented using the instrument angle orienting system to target different spatial locations in the prostate. In certain embodiments, the anatomical sensing system-guided prostate procedure device, and specifically the angle orienting system in conjunction with the convergence point directs a location in three-dimensions of a distal end or tip of the instrument, with the distal end being the end closest to the subject.

In specific embodiments, Magnetic Resonance images of the pelvic area are acquired in the sagittal plane allowing visualization of the pelvis with the device in place. Using MRI visible reference points on the device, the device's precise location with respect to the subject is determined, for example the device's vertical plane and horizontal plane are located. By examining images of the prostate both in the horizontal and vertical planes with respect to the device areas of suspect prostate tissue can be identified for a procedure, such as a biopsy. The position of these areas are locked and the angles, both vertical and horizontal, between center of target tissue and central axis of instrument are measured and/or recorded. These angles can be translated through the convergence point to the instrument angle orienting system. In this way, instrument angle orienting system can be used to guide the biopsy needle to the precise location within the prostate that was identified on the MRI images.

In certain embodiments, the angle orienting system directs a penetration depth of a distal end or tip of the instrument. In certain embodiments, this is accomplished using an instrument that has depth indication, such as on the shaft of the instrument. Alternatively, or even coincidently, the entire device can be monitored in real time by the anatomical sensing system to determine the depth of penetration, insertion or a combination thereof. In certain embodiments, the angle orienting system includes a locking member or other device that retains the instrument at the selected depth. In certain embodiments, the instrument can be passed through the target tissue such that the side of the instrument is within the target tissue. This may be particularly useful for needles with sidewall access or even a digital camera.

In certain embodiments, the anatomical sensing system-guided prostate procedure device includes an instrument guide. In certain embodiments, the instrument guide is substantially cylindrical or ovoid. Other shapes are contemplated, such as faceted, for example square or hexagonal, without departing from the scope of this disclosure. In certain embodiments, the instrument guide extends distally from the convergence point, such as from the distal side of the spherical targeting ball. In certain embodiments, the instrument guide extends from the proximal side of the convergence point, such as from the proximal side of the spherical targeting ball. In certain embodiments, the instrument guide is adjustable and can be positioned against the outer wall of the rectum adjacent to the prostate. In embodiments, the instrument guide allows the instrument, such as a biopsy needle, to slide or otherwise pass through the device. In certain embodiments, the instrument guide is coupled to the spherical targeting ball and extends distally from the spherical targeting ball, such that rotation of the spherical targeting ball orients the instrument guide. In certain embodiments, the instrument guide extends from the proximal side of the spherical targeting ball, for example in addition to the distal extension. In embodiments, the distal tip of the instrument guide includes an anatomical sensing system visible marker that can be used to indicate the position of the distal tip of the instrument guide within image obtained with an anatomical sensing system. This feature can be used as a fiducial marker during system registration and targeting, for example using imaging software the position of this feature of the device can be used to define the location of the device in multiple dimensions, such as three-dimensions with respect to one or more of the patient, and the anatomical sensing system in which the device is being used.

Figure 16:
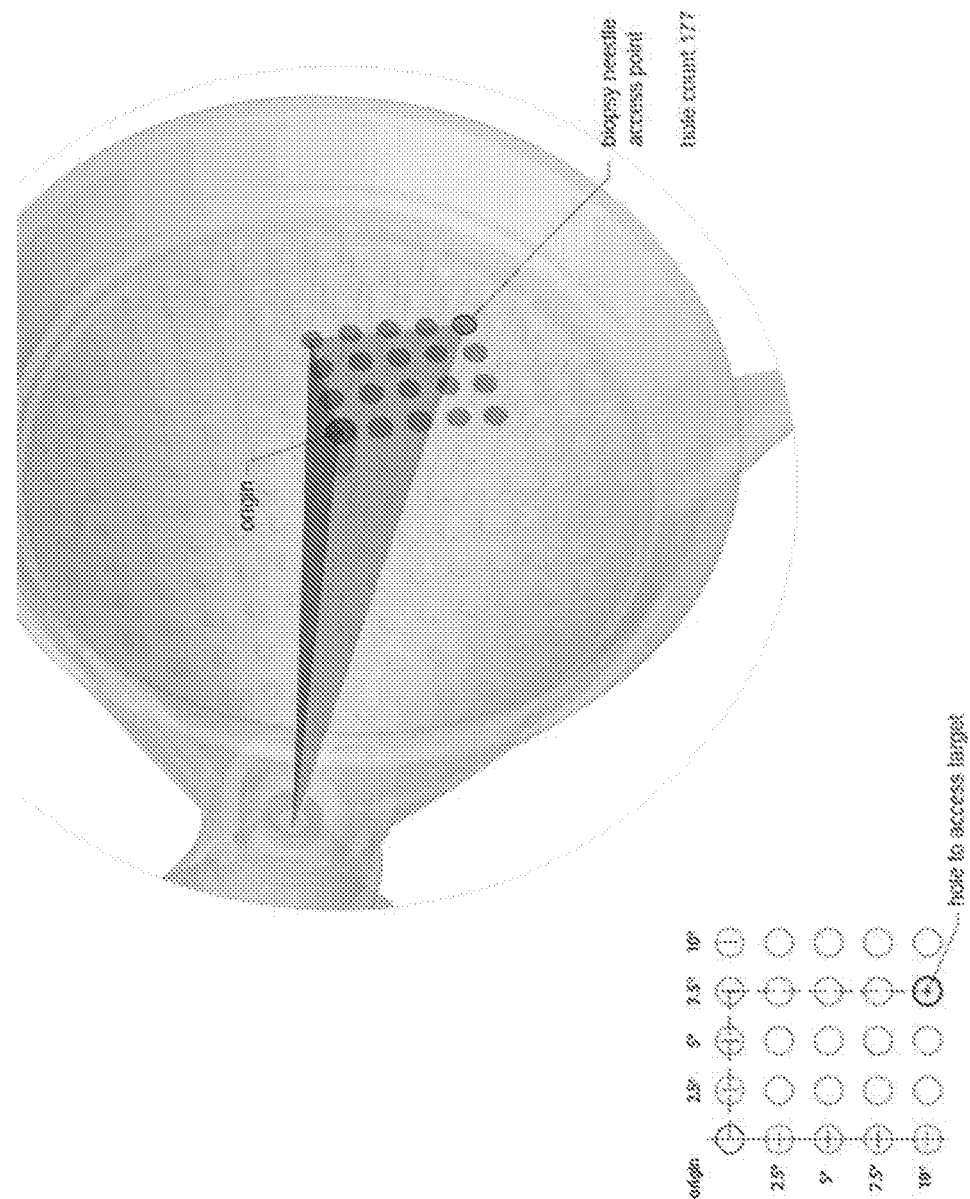
FIG. 16 is a perspective view schematic showing the angles of a suspicious section of prostate mapped to a grid plate of an anatomical sensing system-guided prostate procedure device and a map of the grid plate, in accordance with various embodiments.

In certain embodiments, the instrument angle orienting system comprises a fixed array instrument angle orienting system. In certain embodiments, the fixed array instrument angle orienting system includes a grid array plate disposed within the proximal housing near the proximal end. In embodiments, the grid array plate has a plurality of instrument access channels each with a channel axis and oriented such that channel axis converges to the convergence point. In this way an instrument placed in one of the access channels would be directed to the convergence point. In certain embodiments, the fixed array instrument angle orienting system includes a curved fixed array instrument angle orienting system. In certain embodiments, a curved fixed array instrument angle orienting system includes a curved grid array plate with a convex proximal surface. Alternatively, the curved fixed array instrument angle orienting system includes a curved grid array plate with a concave proximal surface. The distal surface of the curved fixed array instrument angle orienting system maybe convex, concave or even flat. This grid array plate is situated within the open proximal end of the proximal housing section such that the proximal surface of the grid array plate is accessible from outside the device. As mentioned above the grid array plate is perforated by a plurality of regularly spaced instrument access channels, such as biopsy needle access channels, that are oriented such that the axes of all the access channels converge distally at the convergence point. It is understood that the number and arrangement of the instrument access channels in the fixed array may be varied according to the device passed through them. FIG. 16 shows one embodiment with 177 instrument access channels or openings in a grid pattern. If desired, the instrument access channels could be oriented in a series of concentric circles or other pattern. Different embodiments may include arrays with from about 100 to about 200 instrument access channels, from about 150 to about 200 instrument access channels, from about 175 to about 200 instrument access channels, from about 150 to about 250 instrument access channels, from about 200 to about 400 instrument access channels, from about 200 to about 300 instrument access channels, from about 200 to about 250 instrument access channels, from about 300 to about 400 instrument access channels, from about 300 to about 350 instrument access channels, and other ranges, as needed. In embodiments, the spacing of the access channels is between about 1 degree and about 5 degrees as measured from the longitudinal axis of the device, such as about 1.0, 1.1, 1.2, 1.3, 1.4, 1.5, 1.6, 1.7, 1.8, 1.9. 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 degrees, any fractions thereof, and any subset and ranges thereof. In embodiments, the instrument access channels are substantially cylindrical or ovoid in shape and slightly oversized as compared to the instrument, such as a biopsy needle. Other shapes are contemplated, such as faceted, for example square or hexagonal, without departing from the scope of this disclosure. The grid array plate may also have rotatable grid plate cover. In some embodiments, the rotatable grid plate cover has a pie-shaped cutout to allow access to a subset of the access channels. The rotatable grid plate cover may be rotated manually about a bushing or bearing at center of the grid array plate, for example using a grid plate cover handle. Alternatively it may rotate in a groove located about the proximal housing section. In certain embodiments, the pie-shaped section cut out is between about 180 degrees and about 30 degrees. In embodiments, the center of the grid array plate, such as on or about the bushing, may be marked with an anatomical sensing system visible marker that can be used to indicate the position of the center of the grid array plate within image obtained with an anatomical sensing system. This feature can be used as a fiducial marker during system registration and targeting, for example using imaging software the position of this feature of the device can be used to define the location of the device in multiple dimensions, such as three-dimensions with respect to one or more of the patient, and the anatomical sensing system in which the device is being used.

The disclosed device is designed to be imaged concurrently with the prostate such that there is no need to fuse one imaging modality with another. That is, the patient will be scanned with the device fixed in position, in the rectum, and the device will remain stationary during the entirety of the imaging and biopsy procedure. By examining the resulting images either visually or with computer guidance, the user, such as a physician, performing the procedure can select the channel(s) that are best aligned with the target (visible on the same images) and calculate the necessary depth of instrument to get the instrument to the leading edge of the target. In certain embodiments, an appropriately programmed computer is used to determine the channel for use and the depth the instrument needs to be inserted to perform the procedure. For example, radiologists are accustomed to calculating the depth of needle insertion for biopsies in this fashion using standard software, and biopsy needles generally come with one centimeter markings on the shaft to facilitate this process.

In alternate embodiments, the instrument angle orienting system comprises a continuously variable coordinate instrument angle orienting system. In certain embodiments, the continuously variable coordinate instrument angle orienting system comprises a Cartesian coordinate instrument angle orienting system. In certain embodiments, the continuously variable coordinate instrument angle orienting system comprises a cylindrical coordinate instrument angle orienting system.

In certain embodiments, the continuously variable coordinate instrument angle orienting system includes an indexing carriage located at the proximal end of the housing. In embodiments, the indexing carriage is constrained to move along a linear rail assembly. In embodiments, the linear rail assembly is itself constrained to move perpendicularly to the indexing carriage direction, for example along a linear groove. The combination of these features effectively creates a two-axis linear guide system allowing the user to orient the instrument at a desired angle. In certain embodiments, the instrument guide extends proximally from the convergence point to the indexing carriage. This instrument angle orienting system allows the user to orient the needle guide along any desired trajectory by positioning the carriage at Cartesian "XY" coordinates, for example, using a set of graduated markings. In certain embodiments, the indexing carriage includes a pivot bearing at its center and the instrument guide extends from the convergence point to the pivot bearing. In certain embodiments, at the proximal end of the housing the instrument guide extends proximally from the convergence point, for example from the spherical targeting ball, through a pivot bearing housed within the indexing carriage. Advantages of this instrument angle orienting system are that it is infinitely adjustable. In certain embodiments, the instrument guide is adjustable and can be positioned against the outer wall of the prostate and viewed by an anatomical sensing system. The disclosed device is designed to be imaged by an anatomical sensing system concurrently with the prostate such that there is no need to fuse one imaging modality with another. That is, the patient will be scanned with the device fixed in position, in the rectum, and the device will remain stationary during the entirety of the imaging and biopsy procedure.

In certain embodiments, the continuously variable cylindrical coordinate instrument angle orienting system includes a circular plate rotationally disposed within the proximal housing section. In embodiments, the circular plate includes a cutout guide extending radially from its center and an indexing carriage slidably disposed within the cutout guide, and wherein instrument guide extends proximally from the convergence point to the indexing carriage. In certain embodiments, the indexing carriage comprises a pivot bearing and the guide extends from the convergence point to the pivot bearing. In certain embodiments, the continuously variable cylindrical coordinate instrument angle orienting system includes graduated markings representing a radial position and an angular position, for example to specify polar coordinates. In certain embodiments, the instrument guide passes through a translating pivot bearing which is slidably disposed within the cutout guide, such that the cutout can be used to select a specific angle for the instrument with respect to the longitudinal axis of the device. Graduated markings representing radial position and angular position are used to specify a set of polar coordinates that position the proximal end of the instrument guide relative to convergence point such that the instrument trajectory intersects the desired target tissue. Advantages of this needle biopsy indexing system are that it is infinitely adjustable. In certain embodiments, the instrument guide is adjustable and can be positioned against the outer wall of the prostate and viewed with an anatomical sensing system. The disclosed device is designed to be imaged by an anatomical sensing system concurrently with the prostate such that there is no need to fuse one imaging modality with another. That is, the patient will be scanned with the device fixed in position, in the rectum, and the device will remain stationary during the entirety of the imaging and biopsy procedure.

In embodiments, the instrument for use in the disclosed device is a biopsy needle, a probe, a sensor system (for example an ultrasound, camera, or other sensor known in the art), a surgical device (for example an ablation device, such as a laser ablation device), a therapeutic instrument system, or an agent placement device. In certain embodiments, the agent placement device includes a detachable marker, a dye/contrast agent, a drug, or a non-detachable marker. In certain embodiments, the anatomical sensing system-guided prostate procedure device includes one or more points of an anatomical sensing system-detectable agent for locating the device relative to the anatomical sensing system. In certain embodiments, the anatomical sensing system detectable agent includes one or more of a plastic, such as a polycarbonate, a ABS/Polycarbonate blend, a polyester, or a nylon, optionally doped with Barium Sulfate, and/or Titanium Dioxide; a metal, such as Gold, Tantalum, Platinum, Tungsten, Titanium, Cobalt-Chromium, stainless steel, Iron-Chromium-Nickel, zirconium, and alloys thereof; a liquid contrast agent; water; a hydrogel; a thin wire weaving or patterning; or combinations thereof. In certain embodiments, one or more of the points of an anatomical sensing system detectable agent are located at a distal end of the instrument guide. In certain embodiments, one or more of the points of an anatomical sensing system detectable agent are located at the convergence point. In certain embodiments, one or more of the points of an anatomical sensing system detectable agent are located at the center of the instrument angle orienting system. In certain embodiments, one or more of the points of an anatomical sensing system detectable agent are located at one or more of the needle guide tip, the spherical targeting ball, and a center bushing or bearing within the instrument angle orienting system.

In certain embodiments, the anatomical sensing system-guided prostate biopsy includes one or more MRI coils. The inclusion of an MRI coil in the proximity of the prostate greatly increases the quality of the data obtained and hence the quality of MRI images of the prostate and regions of the body in close proximity thereto. An MRI coil can be placed in various spots within or on the exterior of the device. In certain embodiments, the device includes an endorectal MRI coil disposed within the distal end of the housing. This placement puts the coil in close contact with the prostate and/or tissues around the same. In certain embodiments, the device includes an MRI coil disposed in the proximal section of the housing. In certain embodiments, the device includes an MRI coil that spans the distal housing section and the mid housing section. In certain embodiments, the device includes an MRI coil disposed within the mid housing section.

By combining an endorectal MRI coil for optimal multiparametric imaging and a multichannel array for MRI targeted biopsy, the present disclosure provides the advantage of combining two separate uncomfortable procedures into a single integrated procedure. This increases both the convenience and efficiency of a biopsy procedure while reducing cost and burden. Current study times are roughly 45-60 minutes (diagnostic MRI) plus 45-60 minutes (in bore biopsy) or 30 minutes (fusion biopsy). The disclosed device and attendant methods would typically reduce study time to a total of approximately 60 minutes (45 for imaging, 15 for biopsy). In addition, the multichannel access allows maximal sampling flexibility. For example, the operator can biopsy targets only, templated systematic 12 core locations only, or both. Images can be rapidly obtained after needle deployment to confirm that the needle has traversed the target. Additional samples can be immediately taken from neighboring channels if needle positioning is suboptimal.

In embodiments, the MRI coil comprises an MRI coil disposed within the distal housing section. In embodiments, the MRI coil comprises an MRI coil disposed on an exterior surface of the proximal end of the housing. In embodiments, the MRI coil comprises an MRI coil traversing the distal housing section and the mid housing section.

Figure 29:
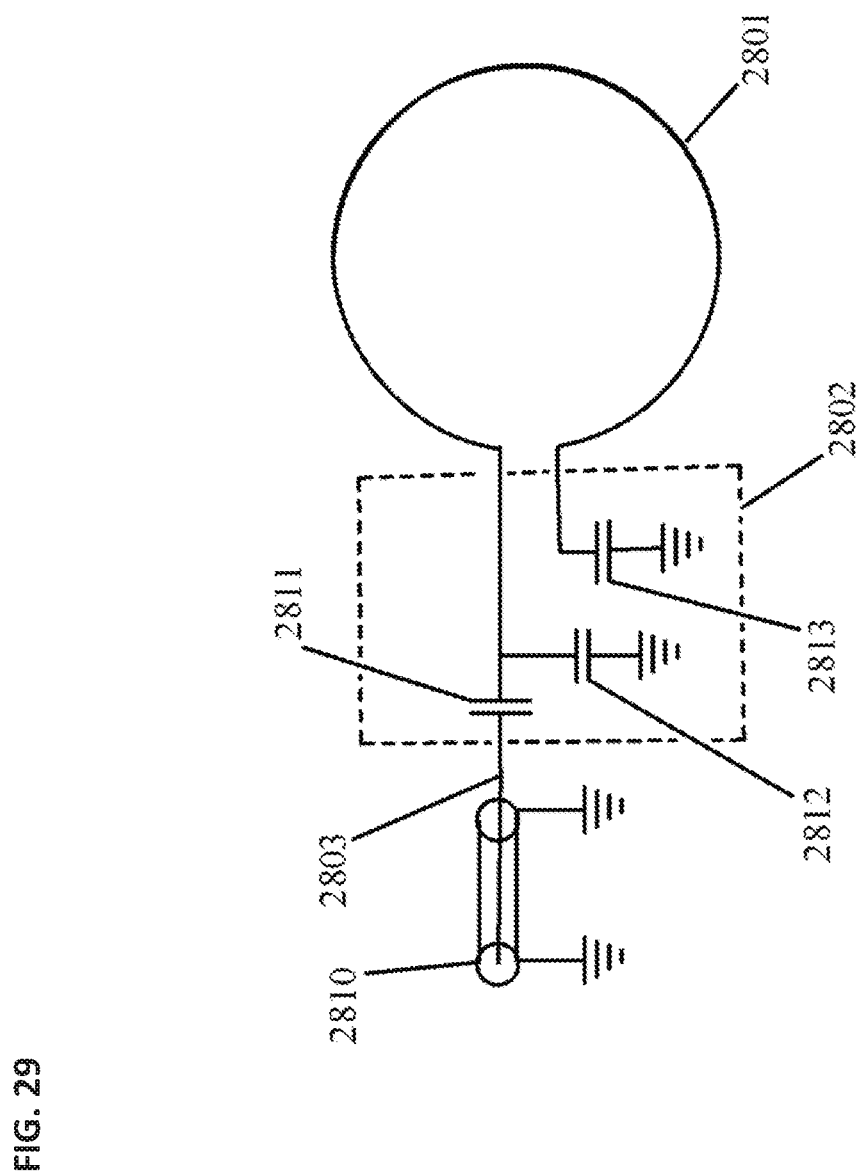
FIG. 29 is a schematic of an exemplary matching circuit, in accordance with various embodiments.
Figure 30:
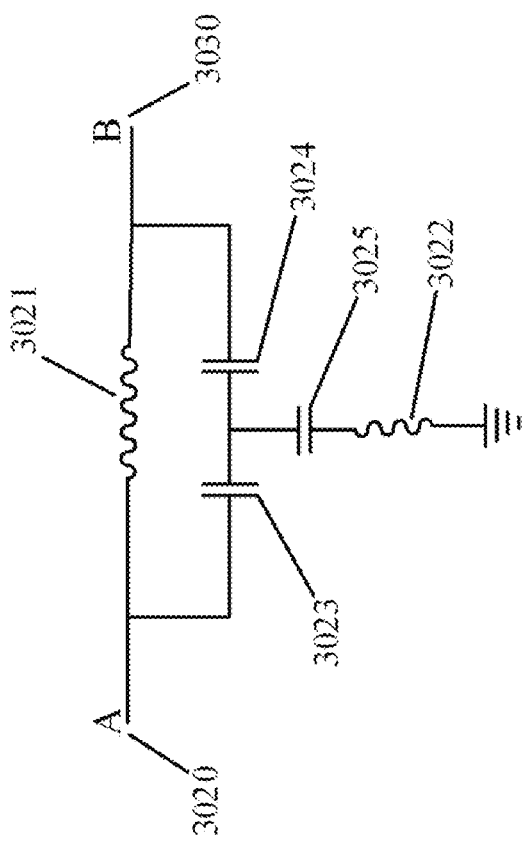
FIG. 30 is a schematic of an exemplary 90 degree phase shift circuit, in accordance with various embodiments.
Figure 31:
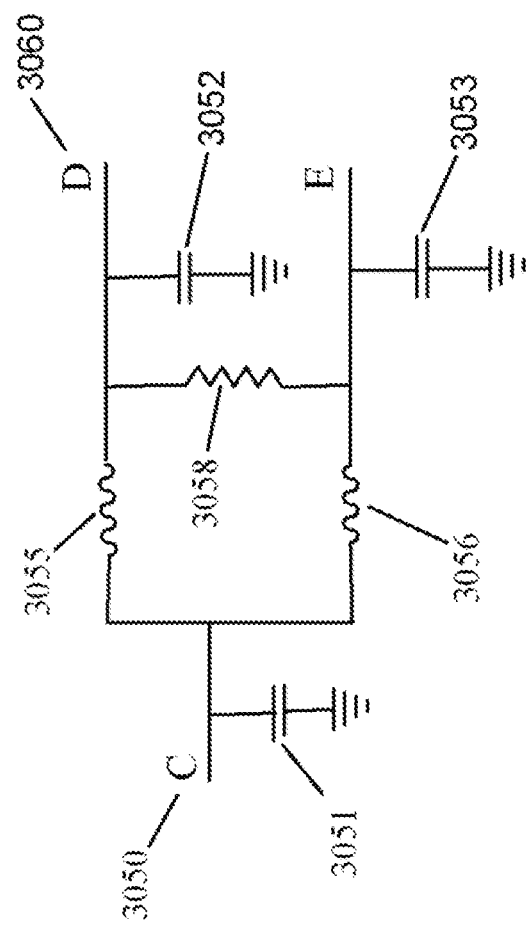
FIG. 31 is a schematic of an exemplary power splitter combiner circuit, in accordance with various embodiments.

In embodiments, the MRI coil includes a loop antenna. In embodiments, the MRI coil includes a butterfly antenna. In embodiments, the MRI coil includes a loop antenna and a butterfly antenna wherein in the loop antenna and the butterfly antenna are driven out of phase by 90 degrees with a phase shifter to create a circularly polarized magnetic field. Thus, in some embodiments, the device and/or system includes a phase shifter. By way of example, endorectal coils are used to improve the signal-to-noise ratio in a MRI image of the prostate. Typical MRI machines used on human subjects create a BO field with a field strength commonly between about 1.5 and 3 Tesla. If one imagines that the BO field is approximately parallel to the z-axis and the length of the human body, and the y-axis is the vertical axis and the x-axis is the horizontal axis perpendicular to the human body, one antenna which can be used is a simple loop which in the orientation of the positioning device detects a magnetic field in y-axis. Alternatively, an antenna with butterfly configuration would detect in the x-axis. Using a combination of the simple loop and the butterfly antenna, the signals detected by these two antenna are combined with a 90 degree phase shift between them. This allows the antenna to detect signals in both the x and y axes. The 90 degree phase shift is comprised of passive components and the signals can be combined, for example to increase signal-to-noise approximately by a square root of two. An exemplary 90° phase shift circuit is shown in FIG. 30. In embodiments, the imaging coil includes a loop antenna, matching components and a signal wire. In embodiments, the imaging coil includes a butterfly antenna, matching components and a signal wire. An exemplary matching circuit and components is shown in FIG. 29. In embodiments, the imaging coil includes the loop antenna, matching components, and a signal wire are interspaced with the butterfly antenna, matching components, and a signal wire. These dual antennas are driven with out of phase by 90 degrees with phase shifter. In embodiments, this composite imaging coil further includes a power splitter/combiner to manage the power and combine the signal from the loop antenna and the butterfly antenna. An exemplary power splitter combiner is shown in FIG. 31. In embodiments the disclosed coils are receiving signal at 123.258 MHz on a 3 Tesla MRI machine. In embodiments, the antenna is driven by differential input. In embodiments, the antenna is driven by single ended input.

In embodiments, the anatomical sensing system-guided prostate procedure device includes a flexible circuit that runs proximally from the imaging coil in the distal housing section through the mid housing section to the proximal housing section, where it couples to an interface board. The interface board is couplable to a complementary board on the sleeve. The materials of the flexible circuit are selected such that they are thin enough to pass through the construction at the mid housing section. In embodiments, the flexible circuit comprises thin metal strips on a polymer substrate. In certain embodiments, the metal comprises copper and the substrate comprises polyimide.

In embodiments, the device and system are designed so that no dedicated software is likely to be required. Radiology images are routinely stored and viewed on a picture archiving and communication system (PACS). Irrespective of vendor, standard PACS tools should be sufficient for biopsy planning, since these allow calculation of required angulation in sagittal and oblique axial planes (multiplanar reformation and goniometer tools) and calculation of required needle insertion depth (linear distance measurement tool). These are routine three-dimensional tasks already familiar to any radiologist who performs image-guided biopsies.

In embodiments, the disclosed device reduces prostate biopsy to a single procedure and allows for targeted collection of suspect tissue. In embodiments, the disclosed device is designed to be imaged by MRI concurrently with the cancerous tissue regions such that there is no need to fuse one imaging modality with another.

Systems including a disclosed device are contemplated. In embodiments, the system includes an instrument for conducting a medical procedure. In embodiments, the instrument is a biopsy needle, a probe, sensor system, surgical device, therapeutic instrument system, or an agent placement device. In embodiments, the agent placement device includes a detachable marker, a dye/contrast agent, a drug, or a non-detachable marker. In embodiments, the instrument includes an anatomical sensing system detectable marker at a distal end. In embodiments, the instrument includes a depth indicator. In embodiments, the system further includes a clamp configured to retain the device stationary relative to the anatomical sensing system.

Disclosed is a method of performing anatomical sensing system-guided procedure on a subject's prostate. In certain embodiments, the method includes: introducing the distal end of a disclosed anatomical sensing system-guided prostate procedure device into the rectum of a subject in proximity to a prostate of the subject; obtaining data on the anatomical features of the subject, including the prostate, and the anatomical sensing system-guided prostate procedure device using an anatomical sensing system; establishing the position of the device and the prostate; determining the location in three-dimensional space of tissue on or within the prostate for the procedure; translating the location in three-dimensional space to the instrument angle orienting system; and using the instrument angle orienting system to guide the instrument to the site of the prostate, thereby preforming the procedure. In certain embodiments, the procedure is a biopsy and the instrument is a biopsy needle, and wherein the tissue on or within the prostate is selected for biopsy at least partially by the data obtained with the imaging device, the method including obtaining a biopsy sample. In certain embodiments, the instrument comprises a biopsy needle, a probe, sensor system, surgical device, therapeutic instrument system, or an agent placement device. In certain embodiments, the agent placement device includes a detachable marker, a dye/contrast agent, a drug, or a non-detachable marker and the procedure includes placing the dye/contrast agent, the drug, or the non-detachable marker at the tissue on or within the prostate. In certain embodiments, the instrument includes an anatomical sensing system detectable marker at a distal end. In certain embodiments, the instrument includes a depth indicator. In certain embodiments, the method includes retaining the device stationary relative to the anatomical sensing system. In certain embodiments, the method includes obtaining images with the anatomical sensing system during the procedure. In embodiments, the method includes introducing the distal end of the anatomical sensing system-guided prostate procedure device, such as disclosed herein into the rectum of a subject in proximity to a prostate of the subject and obtaining images of the device within the subject. In certain embodiments, the position of the device and the prostate is established. In embodiments, the method includes determining the location in three-dimensional space of tissue on or within the prostate for the procedure. In embodiments, the method includes translating the location in three-dimensional space of said tissue to the instrument angle orienting system. In embodiments, the method includes using the instrument angle orienting system to guide the instrument to the site of the prostate, thereby preforming the procedure.

In embodiments, high quality endorectal images are obtained for both diagnosis and biopsy. Currently, in a two stage procedure, images obtained during direct anatomical sensing system-guided biopsy (where no endorectal imaging coil present) are of lower quality than those obtained during the preceding diagnostic endorectal MRI. As a result, the target may not be well visualized and the operator may be forced to estimate target location based on correlation with more clearly visible anatomic landmarks such as the urethra, verumontanum, or distinctive nodules of benign prostatic hyperplasia.

An aspect of the disclosed device is that it minimizes movement of target tissue during image acquisition and biopsy. Because the disclosed device remains stationary in the rectum during the procedure, the risk of prostate deformation and associated target displacement is minimized. This also improves image quality when compared to the industry standard balloon expandable endorectal coil, since anorectal contractions around this coil can result in motion artifact that degrades the quality of the endorectal MR images.

In certain embodiments, the procedure is a biopsy and the instrument is a biopsy needle, and the tissue on or within the prostate is selected for biopsy at least partially by the images obtained with the imaging device, the method further comprising obtaining a biopsy sample. In certain embodiments, the instrument is a probe, or an agent placement device. In certain embodiments, the agent placement device includes a detachable marker, a dye/contrast agent, a drug, or a non-detachable marker and the procedure includes placing the dye/contrast agent, the drug, or the non-detachable marker at the tissue on or within the prostate. In certain embodiments, the instrument includes an anatomical sensing system detectable marker at a distal end. In certain embodiments, the instrument includes a depth indicator. In certain embodiments, the method includes retaining the device stationary relative to the anatomical sensing system. In certain embodiments, the method includes obtaining images with the anatomical sensing system during the procedure.

In embodiments, the clinician has the option to perform either (or both) templated systematic sampling and/or target biopsy sampling of the prostate. In addition, when the instrument angle orienting system is embodied as a curved array, the curvature of the array better conforms to the shape of the prostate, thereby providing fuller coverage of potential target sites than attainable using a planar template. Because the device is designed to be fixed in position (e.g., clamped in place) during use, the distal end of the device remains stationary in the rectum for the entirety of the procedure. This eliminates the problem of prostate deformation during targeting of the biopsy needle, which would necessitate re-acquisition of patient images.

In embodiments, one of the unique features of the disclosed device, system, and methods is that aspects of the device, including those elements of the housing or contained therein are disposable, while other components can be reused. By way of example, the anatomical sensing system-guided prostate procedure device is disposable while elements downstream such as the clamp, compression ring and the electronic features can be reused. By including a coupling between the housing of the anatomical sensing system-guided prostate procedure device and the compression ring, for example, the parts of the system that come in contact with a subject, such as the anatomical sensing system-guided prostate procedure device, can be disposed of after use. In embodiments, the anatomical sensing system-guided prostate procedure device is made of non-costly materials. Those components of the system that do not come in contact with the subject, such as the electronic features of the device (not including the flexible circuit or the antenna(s)), can be retained and used with subsequent procedures or the same or different subjects. These downstream components of the system thus do not need to be made of the same low cost materials as they are not meant to be disposable.

Figure 2:
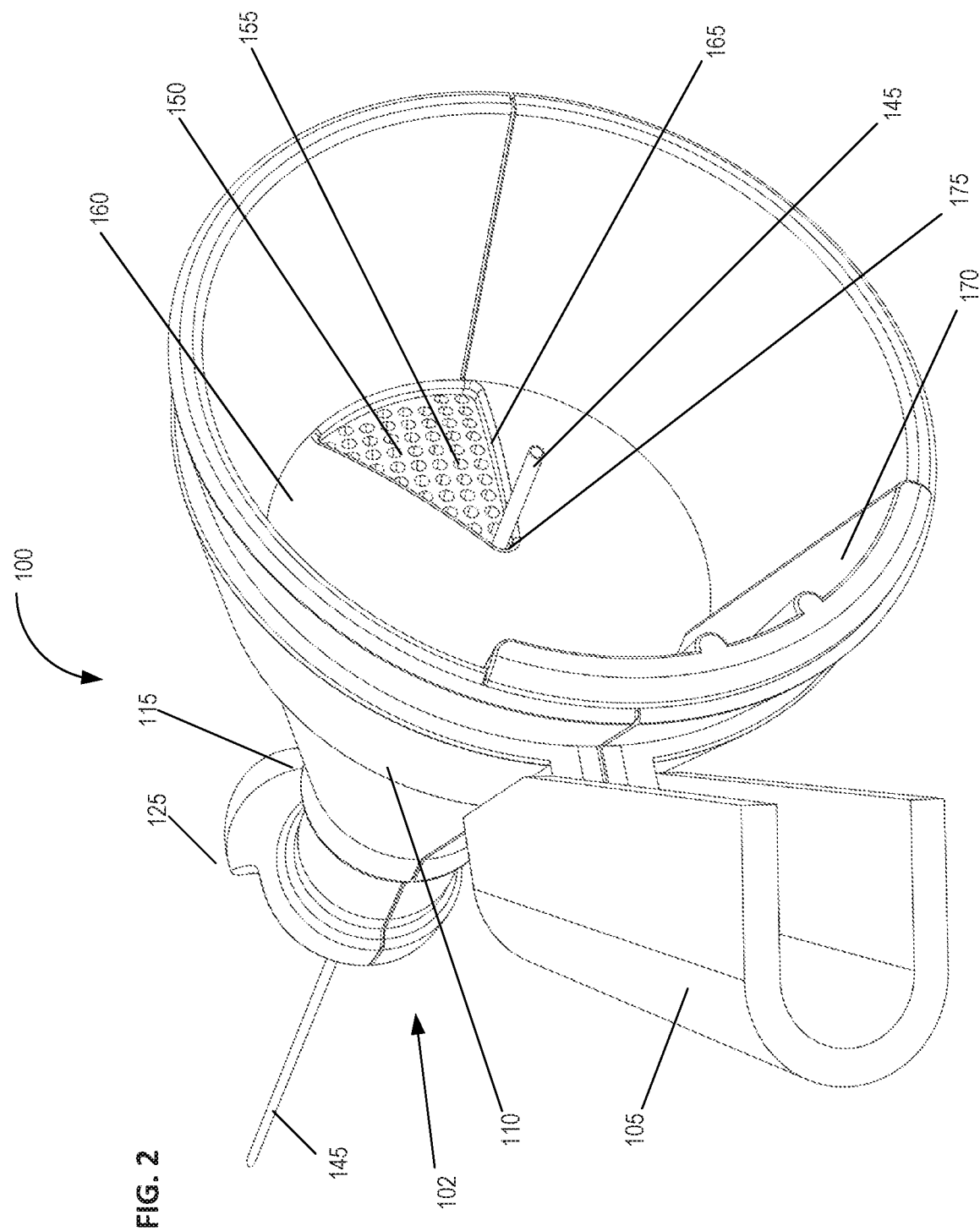
FIG. 2 is a perspective view from the proximal aspect of the anatomical sensing system-guided prostate procedure device shown in FIG. 1, in accordance with various embodiments.
Figure 3:
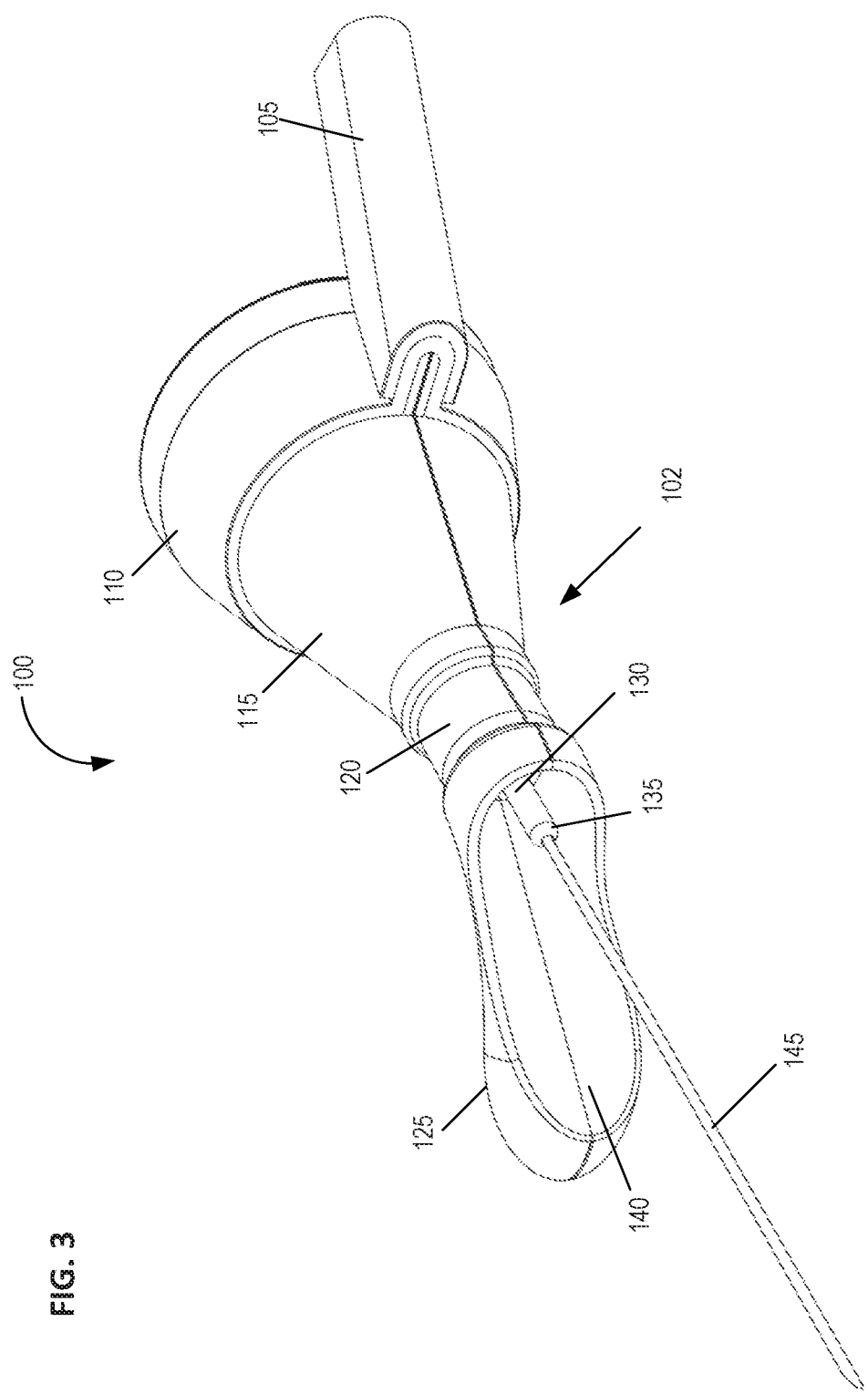
FIG. 3 is a perspective view from the distal aspect of the anatomical sensing system-guided prostate procedure device shown in FIG. 1, in accordance with various embodiments.

FIGS. 1-3 show an embodiment of a disclosed anatomical sensing system-guided prostate procedure device based on a fixed curved array instrument angle orienting system, in accordance with this disclosure. FIG. 1 shows a cross sectional view of an exemplary anatomical sensing system-guided prostate procedure device 100 using a fixed curved array instrument angle orienting system. FIG. 2 shows a perspective view from the proximal aspect of the exemplary anatomical sensing system-guided prostate procedure device 100. FIG. 3 shows a perspective view from the distal aspect of the anatomical sensing system-guided prostate procedure device 100. The device 100 includes a housing 102 comprised of three sections: a proximal housing section 115, a mid housing section 120, and a distal housing section 125. The proximal housing section 115 and mid housing section 120 are centered along a common longitudinal axis. The distal housing section 125 section is angled superiorly away from this axis. A compression sleeve 110 is fitted around the outer surface of the proximal housing section 115 and coupled to a clamp handle 105 on the inferior aspect of the device 100. As shown in FIGS. 20-23 below, the compression sleeve 110 may house power supply connections that mate with connections on the outside surface of the device 100, for example to power an MRI imaging coil (not shown) within the device or on the exterior surface of the device 100. The clamp handle 105 may be used fix the device 100 in a stationary position, for example, by clamping the clamp handle 105 to a table-mounted clamp stand (not shown). As the proximal housing section 115 extends proximally from the mid housing section, it expands to accommodate the fixed curved array instrument angle orienting system.

A curved grid array plate 150 having a convex proximal surface and a concave distal surface is situated within the proximal end of the proximal housing section 115 such that the convex proximal surface is accessible from outside the device 100. The curved grid array plate 150 is perforated by a plurality of biopsy needle access channels 155, each of which is cylindrical in shape and oriented such that the axes of all the access channels 155 converge distally to a common convergence point location 208. The grid array plate 150 may also have rotatable grid plate cover 160 having a pie-shaped cutout 165 to allow access to a subset of the access channels 155 from proximal-to-distal approach (see FIG. 2). The rotatable grid plate cover 160 may be rotated manually about a bushing 175 at the center of the grid array plate 150 using a grid plate cover handle 170. The grid array plate 150 and its set of access channels 155 comprise a section of the instrument angle orienting system for the anatomical sensing system-guided prostate procedure device 100.

The mid housing section 120 of the anatomical sensing system-guided prostate procedure device 100 comprises a recessed waist within which a spherical targeting ball 205 is housed as part of the instrument angle orienting system. The inner surface of the recessed waist has a spherical bearing surface 215, against which the spherical targeting ball 205, centered about a convergence point location 208, may rotate. In embodiments, the spherical bearing surface 215 may contain an anatomical sensing system visible agent compartment 220, for example a contrast agent, such as water/hydrogel, to provide image contrast during MRI imaging. This feature can be used as a fiducial marker during system registration and biopsy targeting, for example using imaging software the position of this feature of the device 100 can be used to define the location of the device in multiple dimensions, such as three-dimensions with respect to one or more of the patient, and the MRI system in which the device 100 is being used. The spherical targeting ball 205 has a conical cutout 210 on its proximal side and a fixed length needle guide 130 on its distal side. In embodiments, the distal tip 135 of the needle guide 130 may include an anatomical sensing system visible agent, for example a contrast agent such as water or hydrogel to cause contrast at that location during MRI imaging. Similar to the anatomical sensing system visible agent in the contrast agent compartment 220, the anatomical sensing system visible agent in the distal tip 135 of the needle guide 130 can be used as a fiducial marker during system registration and biopsy targeting, for example using imaging software the position of this feature of the device 100 can be used to define the location of the distal tip 135 of the needle guide 130 in multiple dimensions, such as three-dimensions with respect to one or more of the patient, and the MRI system in which the device 100 is being used.

FIG. 1 also depicts a biopsy needle 145 passing through one of the access channels 155 of the curved grid array plate 150, entering the conical cutout 210 of the spherical targeting ball 205, and exiting through the fixed length needle guide 130. While the biopsy needle 145 is shown passing through a central access channel 155, it is contemplated that the needle can pass through any of the access channels 155. Together, the access channels 155 of the curved grid array plate 150 and the rotatable spherical targeting ball 205 with the attached fixed length needle guide 130 allow the biopsy needle 145 to be aimed along discrete, predictable trajectories for biopsy targeting.

The distal housing section 125 section of the anatomical sensing system-guided prostate procedure device 100 is angled superiorly away from the centerline of the proximal housing section 115 and mid housing section 120 sections. In embodiments, this angle may be between about 10 and about 45 degrees. The cross-section view of the distal housing section 125 in FIG. 1 shows a distal tip coil compartment 305, an internal compartment within which an imaging coil may be placed to improve MRI imaging in the vicinity of the coil. In some embodiments, a proximal coil 310 may also be attached to the external surface of the proximal housing section 115 to improve MRI imaging quality. As best seen in FIG. 3, on the inferior aspect of the distal housing section 125 section, there is a needle access cutout 140 from which the fixed length needle guide 130 and biopsy needle 145 are deployed. As shown in FIG. 3 the biopsy needle 145 can be seen exiting the fixed length needle guide 130 at the needle access cutout 140.

Figure 5:
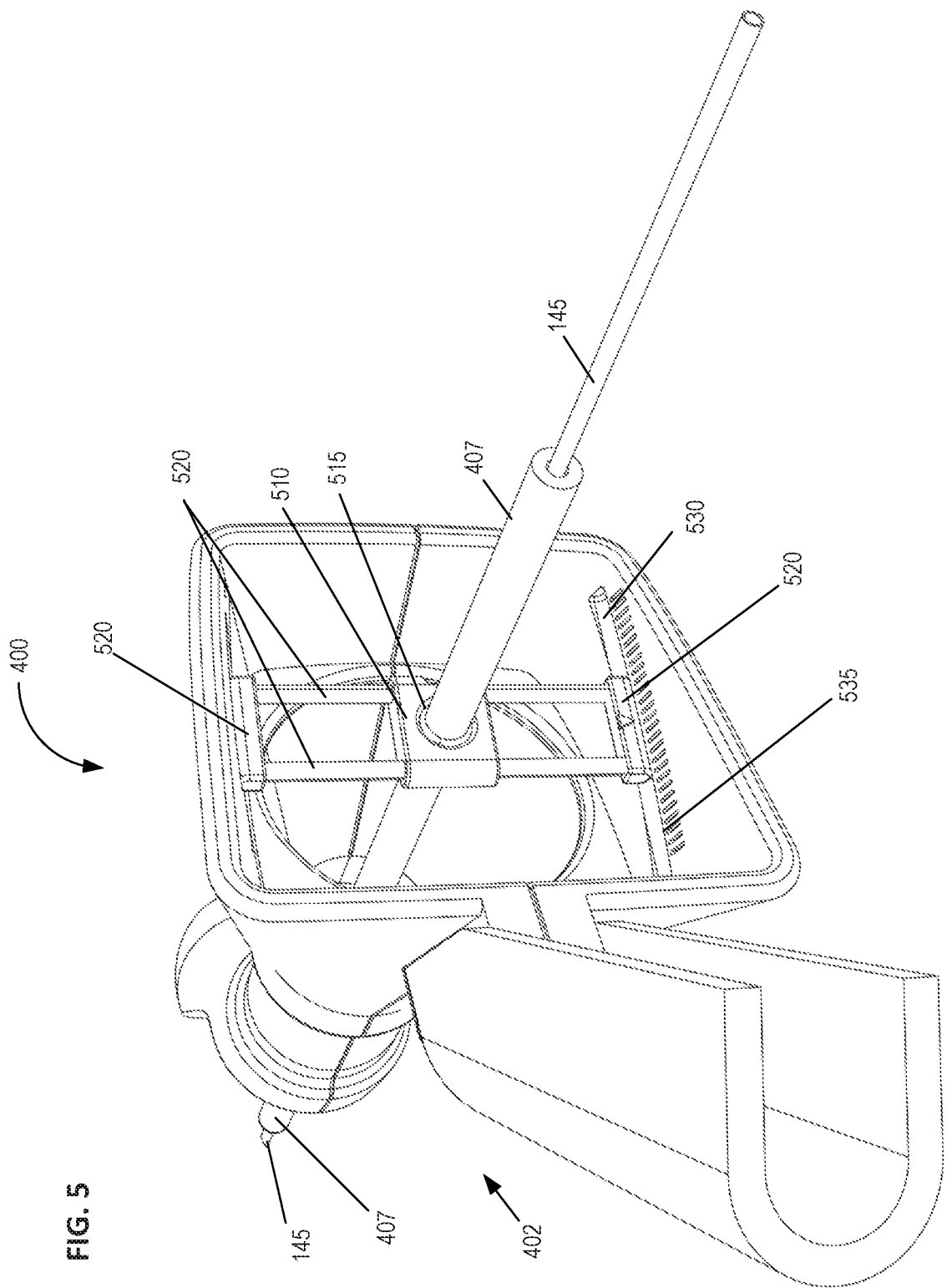
FIG. 5 is a perspective view from the proximal aspect of the anatomical sensing system-guided prostate procedure device shown in FIG. 4, in accordance with various embodiments.
Figure 6:
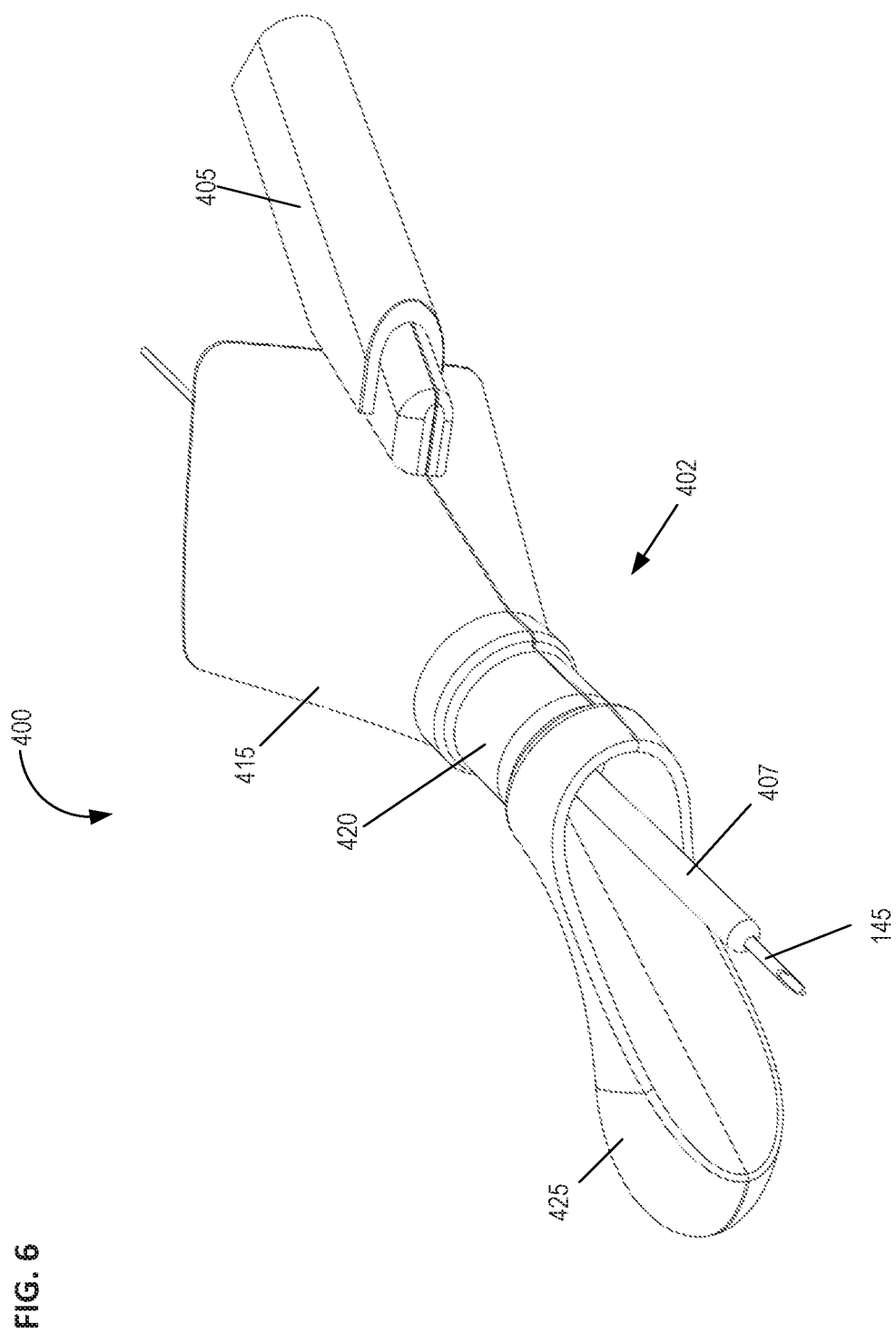
FIG. 6 is a perspective view from the distal aspect of the anatomical sensing system-guided prostate procedure device shown in FIG. 4, in accordance with various embodiments.

FIGS. 4-6 shows an alternate embodiment of a prostate procedure device 400 utilizing a targeting scheme based on a continuously variable Cartesian coordinate instrument angle orienting system rather than a grid array template as shown in the device depicted in FIGS. 1-3. FIG. 4 shows a cross sectional view of an exemplary anatomical sensing system-guided prostate procedure device 400 based on a continuously variable Cartesian coordinate instrument angle orienting system. FIG. 5 shows a perspective view from the proximal aspect of the exemplary anatomical sensing system-guided prostate procedure device 400. FIG. 6 shows a perspective view from the distal aspect of the exemplary anatomical sensing system-guided prostate procedure device 400. Similar to the embodiment shown in FIGS. 1-3, the device 400 includes a housing 402 comprised of three sections: a proximal housing section 415, a mid housing section 420, and a distal housing section 425. The proximal housing section 415 and mid housing section 420 sections are centered along a common axis, and the distal housing section 425 section is angled superiorly away from this axis. In the embodiment no compression sleeve is shown and a clamp handle 405 is coupled to the inferior aspect of the device 400. This clamp handle 405 may be used fix the device 400 in a stationary position, for example, by clamping the clamp handle 405 to a table-mounted clamp stand (not shown). In contrast to the embodiment shown in FIGS. 1-3, the proximal housing section 415 transitions from a round to a square cross-section as it expands proximally. This square cross-section is configured to house the continuously variable Cartesian coordinate instrument angle orienting system.

As best shown in FIG. 5, at the proximal end 415 of the housing 402, the needle guide 505 passes through a pivot bearing 515 housed within a carriage 510 which is constrained to move along a linear rail assembly 520. The linear rail assembly 520 is constrained to move perpendicularly to the carriage 510 direction along a linear groove 530, effectively creating a two-axis linear guide system. This instrument angle orienting system allows the user to orient the needle guide along any desired trajectory by positioning the carriage 510 at the required Cartesian "XY" coordinates using a set of graduated markings 535.

The mid housing section 420 section of the anatomical sensing system-guided prostate procedure device 100 comprises a recessed waist within which a spherical targeting ball 205 is housed as part of the instrument angle orienting system. The inner surface of the recessed waist has a spherical bearing surface 215, against which the spherical targeting ball 205, centered about a convergence point location 208, may rotate. In embodiments, the spherical bearing surface 215 may contain an anatomical sensing system visible agent compartment 220. In this embodiment the biopsy needle 145 travels through a needle guide 405 which extends the full length of the device housing and passes through a ball-biopsy needle targeting pivot assembly at the mid housing section.

The distal housing section of the anatomical sensing system-guided prostate procedure device 400 is angled superiorly away from the centerline of the proximal housing section 415 and mid housing section 420 sections. In embodiments, this angle may be between about 10 and about 45 degrees. The cross-section view of the distal housing section 425 in FIG. 4 shows a distal tip coil compartment 305, an internal compartment within which an imaging coil may be placed to improve MRI imaging in the vicinity of the coil. As best seen in FIG. 6, on the inferior aspect of the distal housing section 425 section, there is a needle access cutout 440 from which the fixed length needle guide 430 and biopsy needle 445 are deployed. As shown in FIG. 6 the biopsy needle 445 can be seen exiting the fixed length needle guide 430 at the needle access cutout 440.

Figure 8:
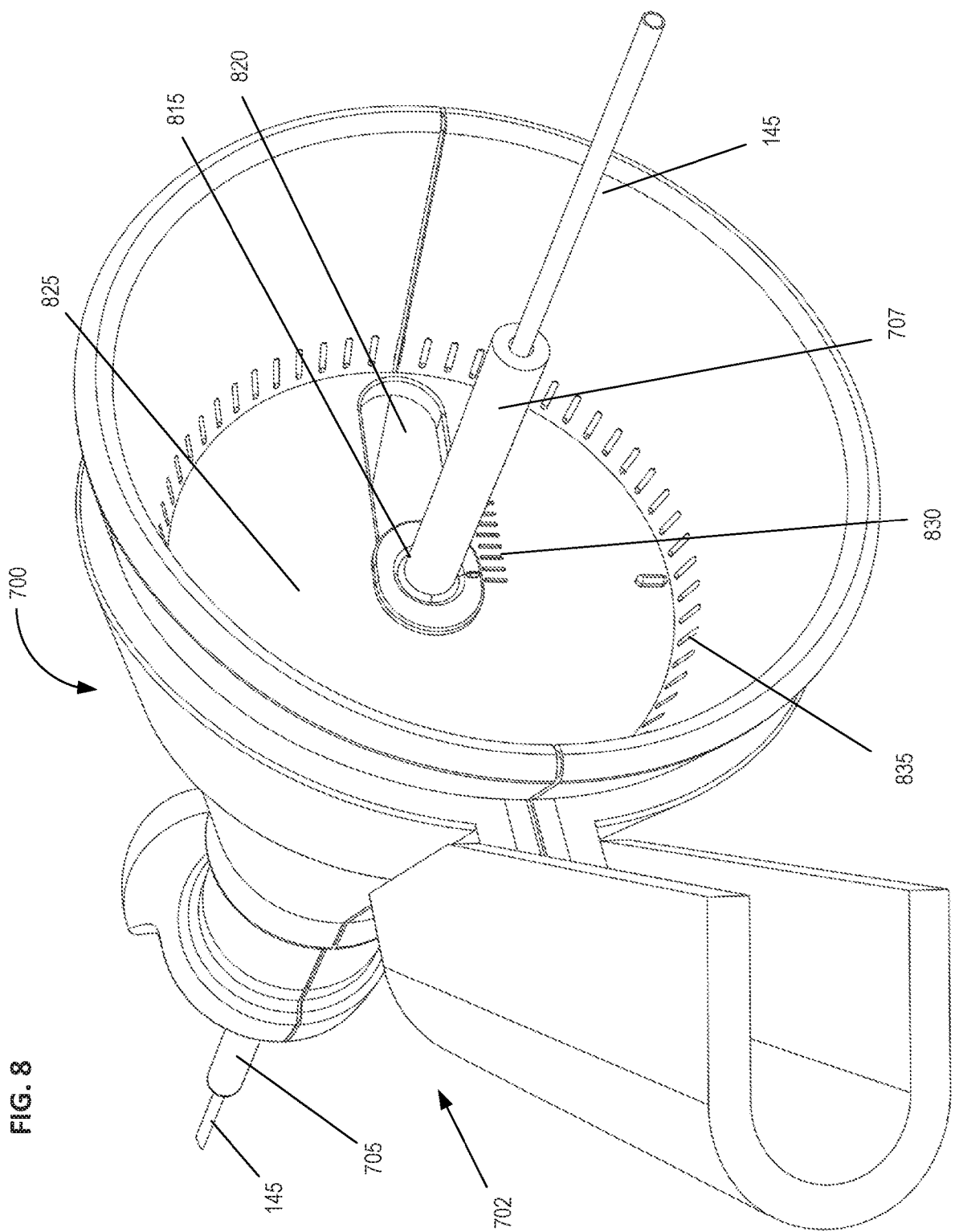
FIG. 8 is a perspective view from the proximal aspect of the anatomical sensing system-guided prostate procedure device shown in FIG. 7, in accordance with various embodiments.
Figure 9:
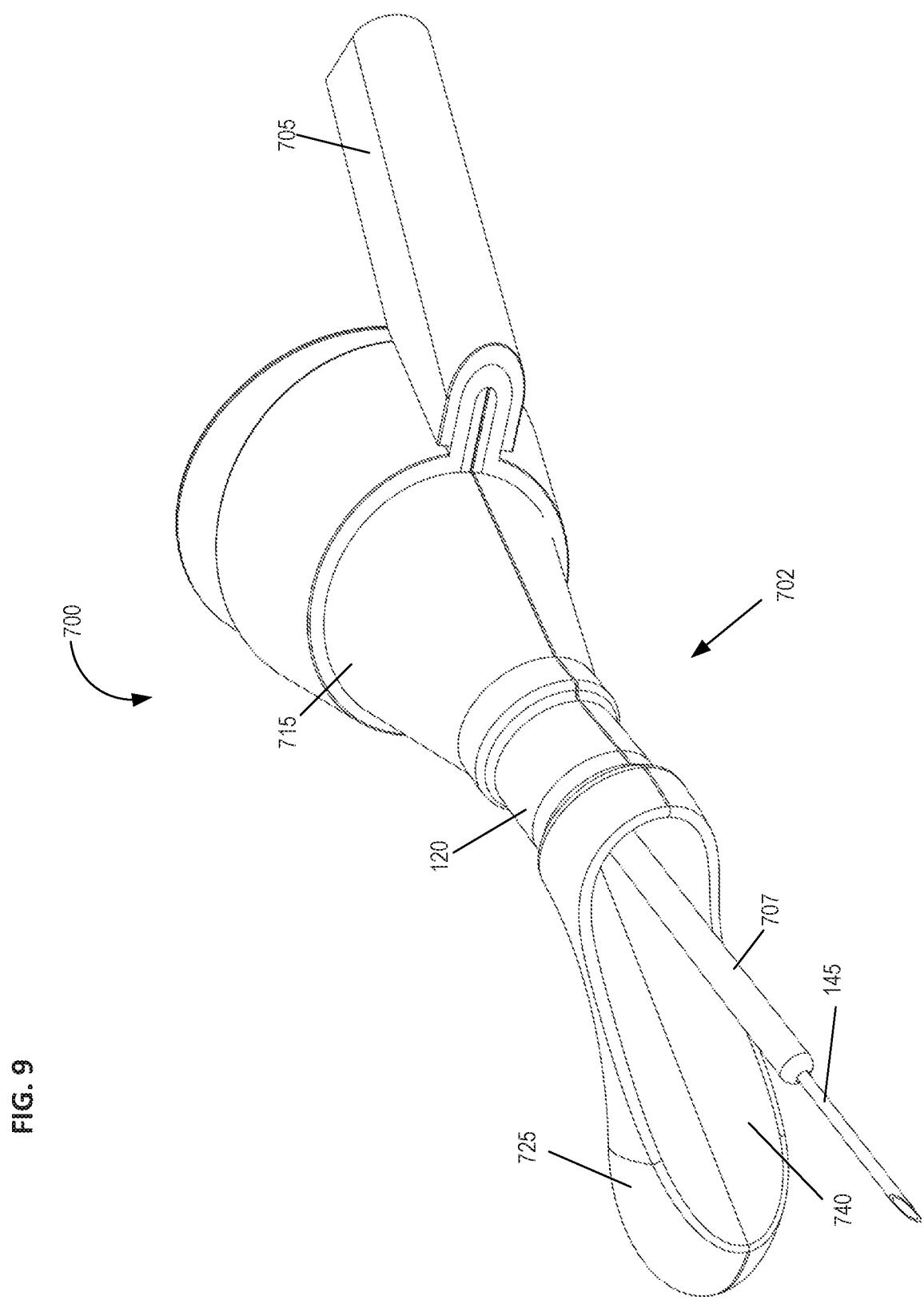
FIG. 9 is a perspective view from the distal aspect of the anatomical sensing system-guided prostate biopsy shown in FIG. 7, in accordance with various embodiments.

FIGS. 7-9 shows an alternate embodiment of a prostate procedure device 400 utilizing a targeting scheme based on a continuously variable cylindrical coordinate instrument angle orienting system rather than a grid array template as shown in FIGS. 1-3 or the Cartesian coordinate system depicted in FIGS. 4-6. FIG. 7 shows a cross sectional view of an exemplary anatomical sensing system-guided prostate procedure device 700 based on a continuously variable cylindrical coordinate instrument angle orienting system. FIG. 8 shows a perspective view from the proximal aspect of the anatomical sensing system-guided prostate procedure device 400. FIG. 9 shows a perspective view from the distal aspect of the anatomical sensing system-guided prostate procedure device 400. The device 700 includes a housing 702 comprised of three sections: a proximal housing section 715, a mid housing section 720, and a distal housing section 725. The proximal housing section 715 and mid housing section 720 sections are centered along a common axis, and the distal housing section 725 section is angled superiorly away from this axis. In the embodiment no compression sleeve is shown and a clamp handle 705 is coupled to the inferior aspect of the device 700. This clamp handle 705 may be used fix the device 700 in a stationary position, for example, by clamping the clamp handle 705 to a table-mounted clamp stand (not shown).

As best shown in FIG. 8, instrument angle orienting system of the device 700 comprises a circular plate 825 that is rotationally disposed within the proximal housing section, the circular plate 825 having a cutout guide 820 extending radially from its center. The needle guide 707 passes through a translating pivot bearing 815 which is slidably disposed within the cutout guide 820. Graduated markings representing radial position 830 and angular position 535 are used to a set of specify polar coordinates that position the proximal end of the needle guide 707 relative to a convergence point location 208 such that the biopsy needle 145 trajectory intersects the desired target tissue.

The mid housing section 720 section of the anatomical sensing system-guided prostate procedure device 700 comprises a recessed waist within which a spherical targeting ball 205 is housed as part of the instrument angle orienting system. The inner surface of the recessed waist has a spherical bearing surface 215, against which the spherical targeting ball 205, centered about a convergence point location 208, may rotate. In embodiments, the spherical bearing surface 215 may contain an anatomical sensing system visible agent compartment 220. In this embodiment the biopsy needle 145 travels through a needle guide 707 which extends the full length of the device housing and passes through a ball-biopsy needle targeting pivot assembly at the mid housing section.

The distal housing section 725 of the anatomical sensing system-guided prostate procedure device 700 is angled superiorly away from the centerline of the proximal housing section 715 and mid housing section 720 sections. In embodiments, this angle may be between about 10 and about 45 degrees. The cross-section view of the distal housing section 725 in FIG. 7 shows a distal tip coil compartment 305, an internal compartment within which an imaging coil may be placed to improve MRI imaging in the vicinity of the coil. As best seen in FIG. 9, on the inferior aspect of the distal housing section 725 section, there is a needle access cutout 740 from which the fixed length needle guide 430 and biopsy needle 145 are deployed. As shown in FIG. 9 the biopsy needle 145 can be seen exiting the fixed length needle guide 707 at the needle access cutout 440.

Figure 10:
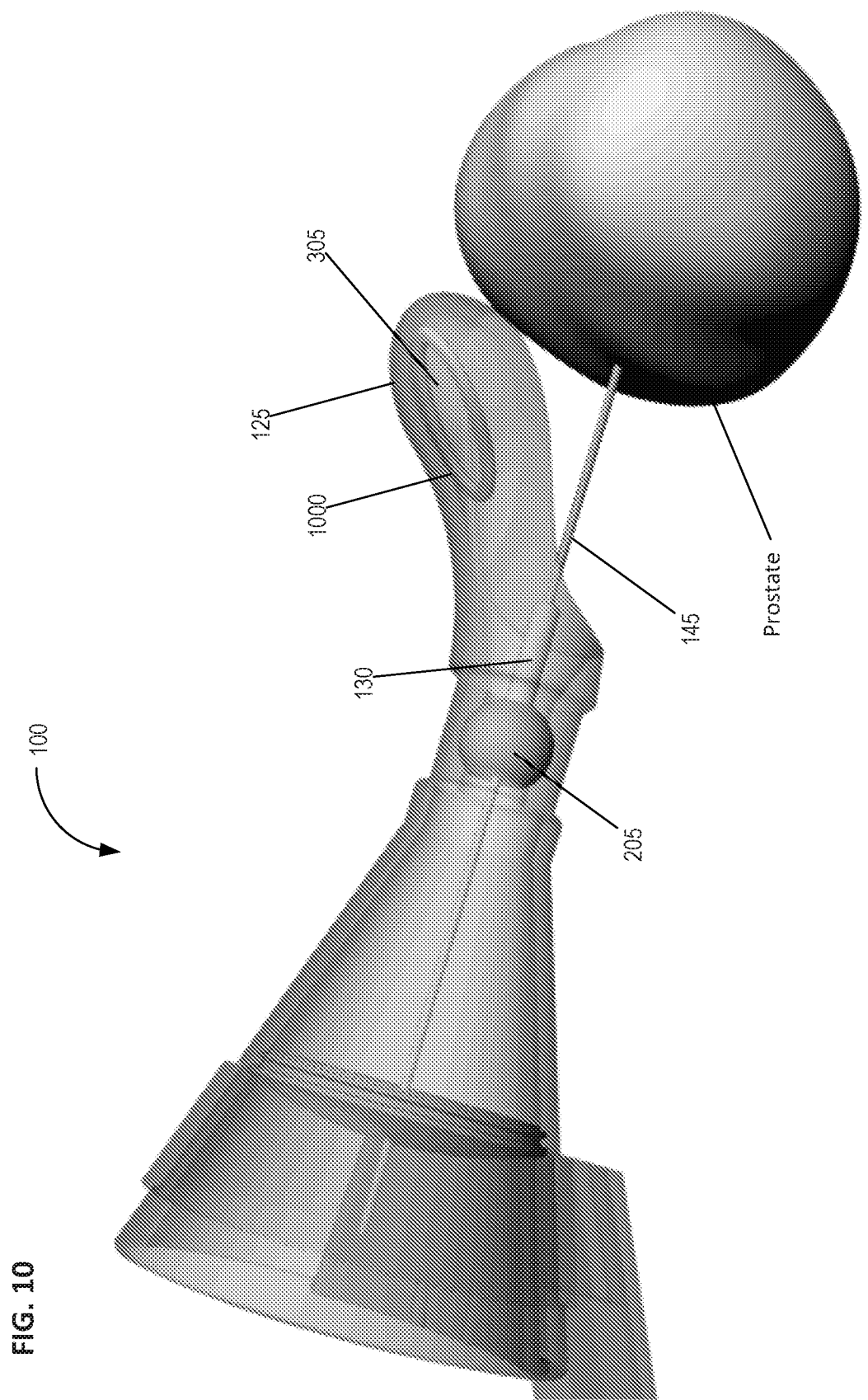
FIG. 10 is partially transparent side perspective view of an anatomical sensing system-guided prostate procedure device showing the placement of an imaging coil in the distal end of the device, in accordance with various embodiments.

FIG. 10 is partially transparent side perspective view of an embodiment of the disclosed anatomical sensing system-guided prostate procedure device 100 showing the placement of an imaging coil 1000 in the distal housing section 125. The imaging coil 1000 is configured to be placed within the compartment 305 of the distal hosing section 125. As shown in FIG. 10 when the device 100 is placed in the rectum of a subject, the imaging coil 1000 is situated endorectally and in close proximity to the prostate which increases the quality of MRI images of the prostate and surrounding tissue. Also shown in this view are the spherical targeting ball 205, the biopsy needle guide 130 and the biopsy needle 145. The biopsy needle 145 is depicted entering the prostate.

Figure 11:
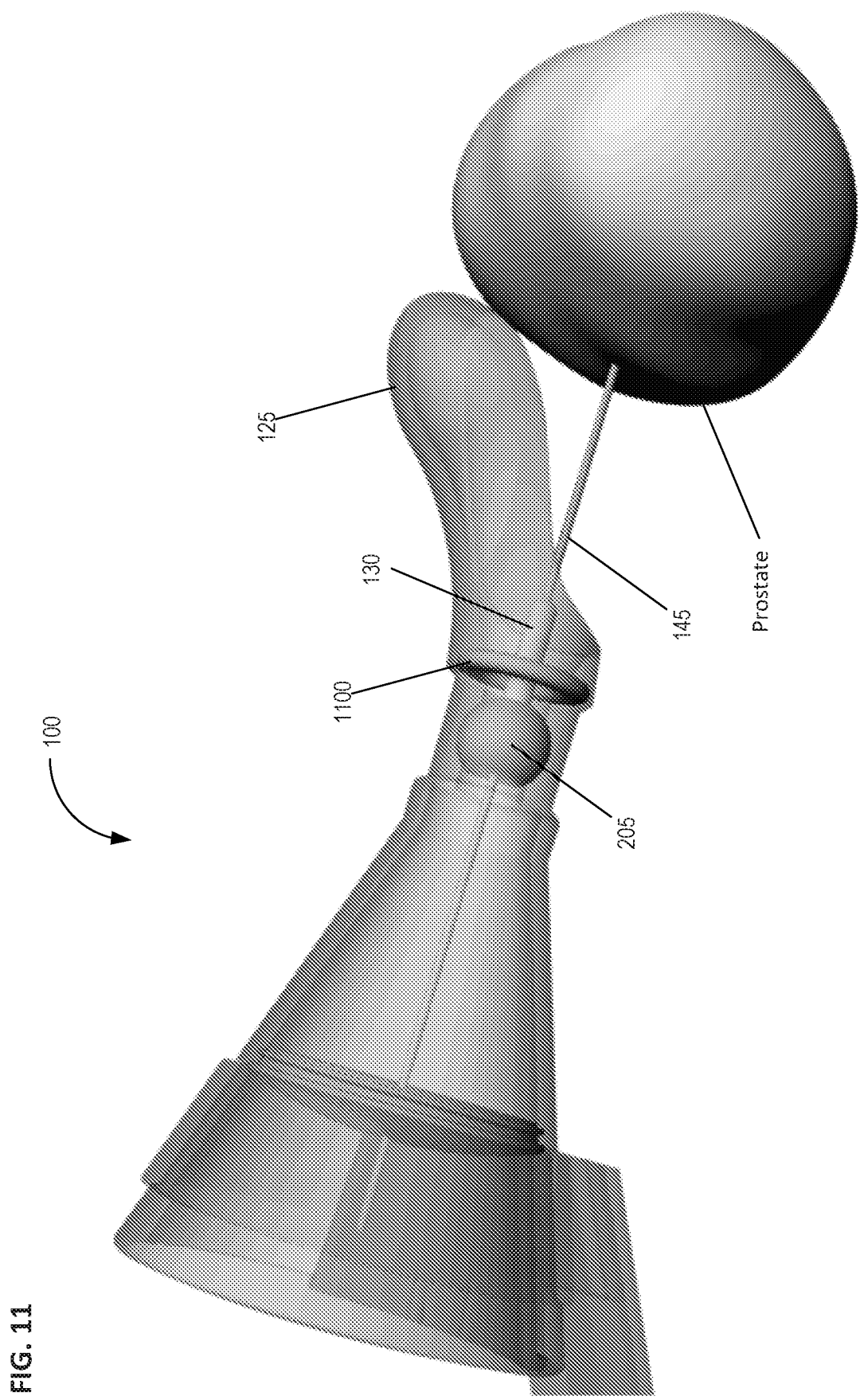
FIG. 11 is partially transparent side perspective view of an anatomical sensing system-guided prostate procedure device showing the placement of an imaging coil just proximal to the distal end of the device, in accordance with various embodiments.

FIG. 11 is partially transparent side perspective view of an embodiment of the disclosed anatomical sensing system-guided prostate procedure device 100 showing the placement of an imaging coil 1100 at the proximal end of the distal housing section 125 of the device 100. As shown in FIG. 11 when the device 100 is placed in the rectum of a subject, the imaging coil 1100 is situated endorectally and in close proximity to the prostate which increases the quality of MRI images of the prostate and surrounding tissue. Also shown in this view are the spherical targeting ball 205, the biopsy needle guide 130 and the biopsy needle 145. The biopsy needle 145 is depicted entering the prostate.

Figure 12:
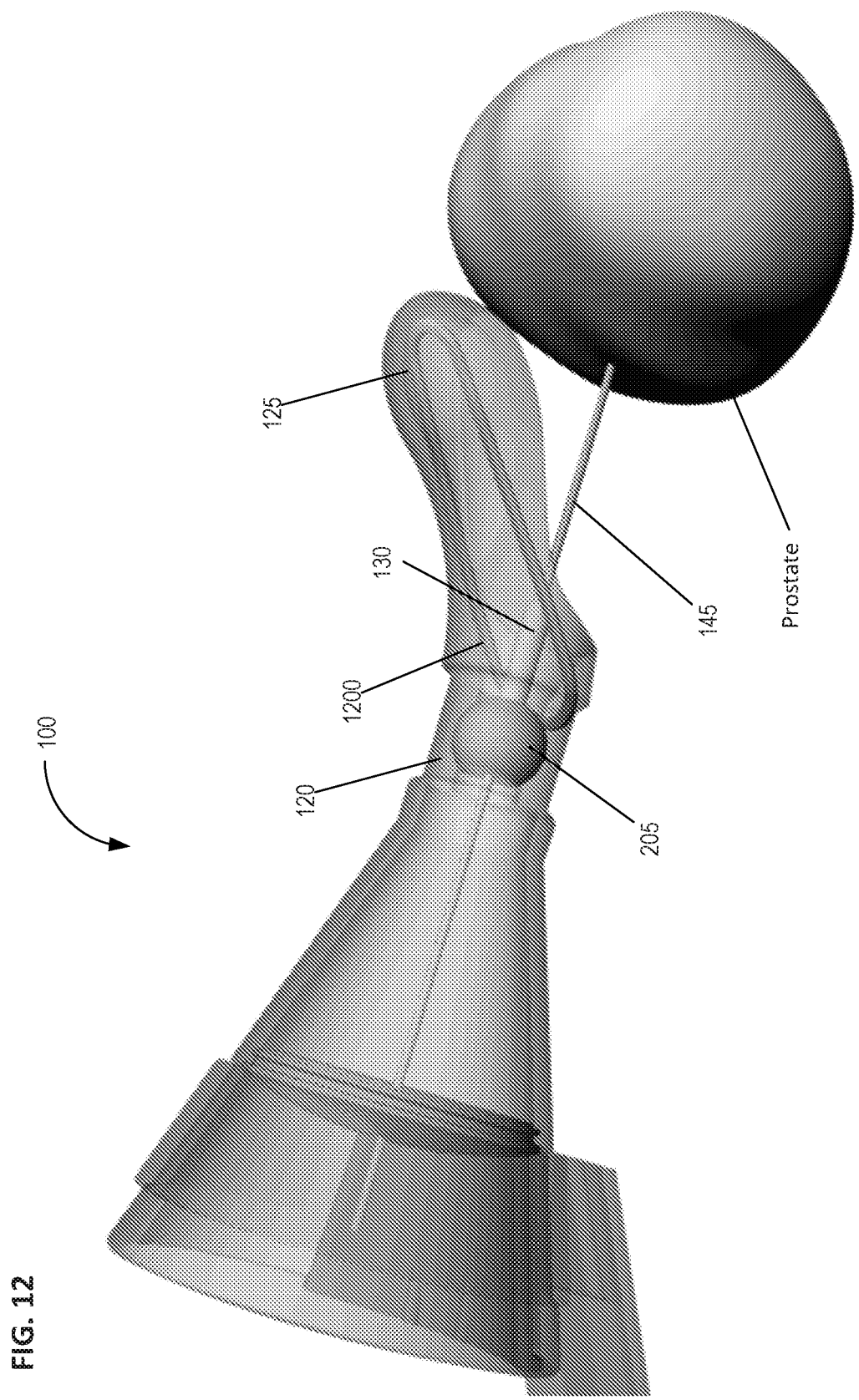
FIG. 12 is partially transparent side perspective view of an anatomical sensing system-guided prostate procedure device showing the placement of an imaging coil traversing the mid housing section and the distal housing section of the device, in accordance with various embodiments.

FIG. 12 is partially transparent side perspective view of an embodiment of the disclosed anatomical sensing system-guided prostate procedure device 100 showing the placement of an imaging coil 1200 traversing the mid housing section 120 and the distal housing section 125 of the device 100. As shown in FIG. 12 when the device 100 is placed in the rectum of a subject, the imaging coil 1200 is situated endorectally and in close proximity to the prostate which increases the quality of MRI images of the prostate and surrounding tissue. Also shown in this view are the spherical targeting ball 205, the biopsy needle guide 130 and the biopsy needle 145. The biopsy needle 145 is depicted entering the prostate.

Aspects of the present disclosure concern anatomical sensing system-guided prostate biopsy using a disclosed device. As disclosed herein the disclosed device is inserted into the patient's rectum and may be secured to the clamp-stand to prevent movement of the device. Aspects of the methods are detailed in FIGS. 13-16.

Figure 13:
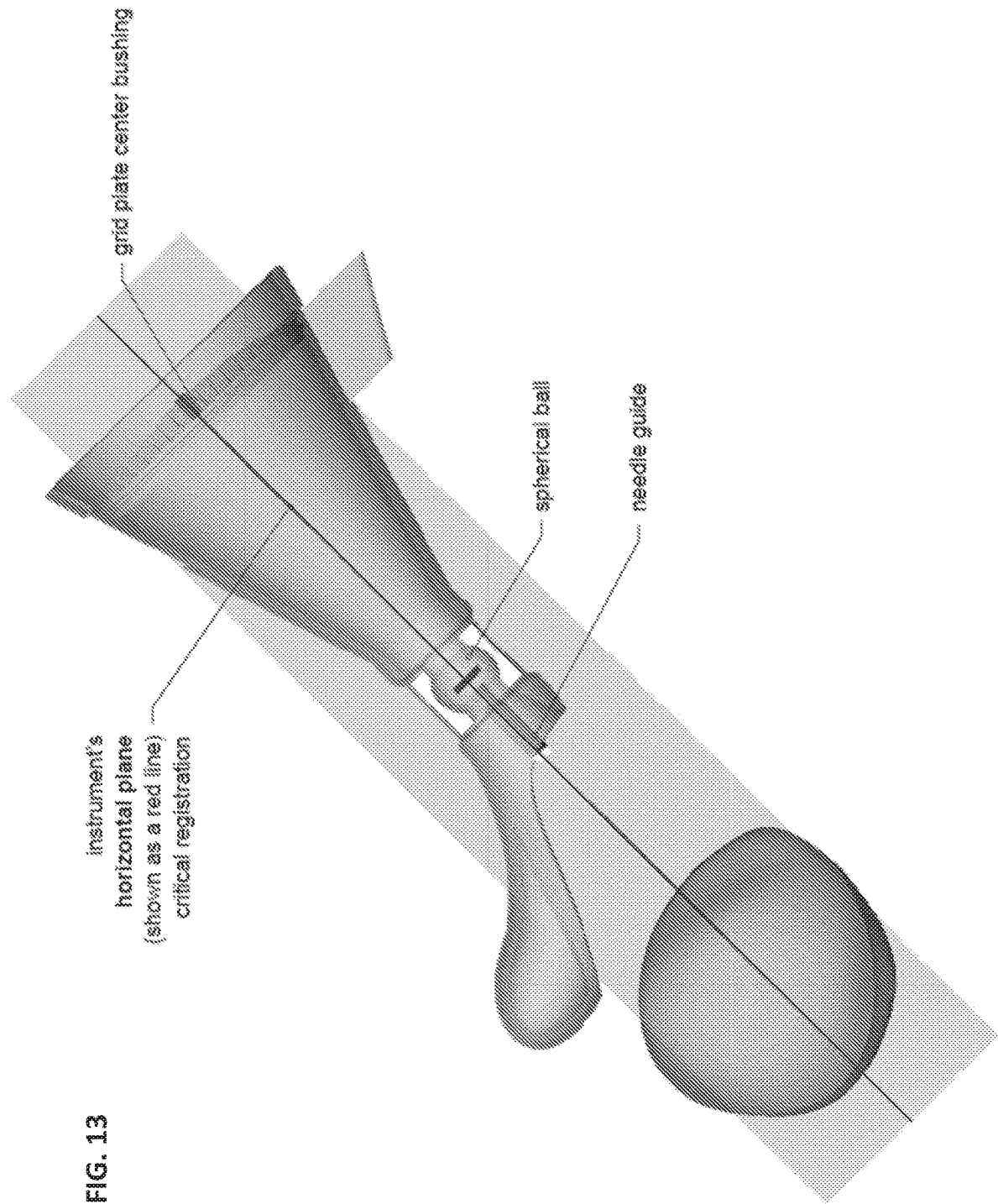
FIG. 13 is a side view schematic showing the orientation of the needle guide, spherical targeting ball, and center bushing relative to the prostate used to define the horizontal plane of the anatomical sensing system-guided prostate procedure device, in accordance with various embodiments.
Figure 14:
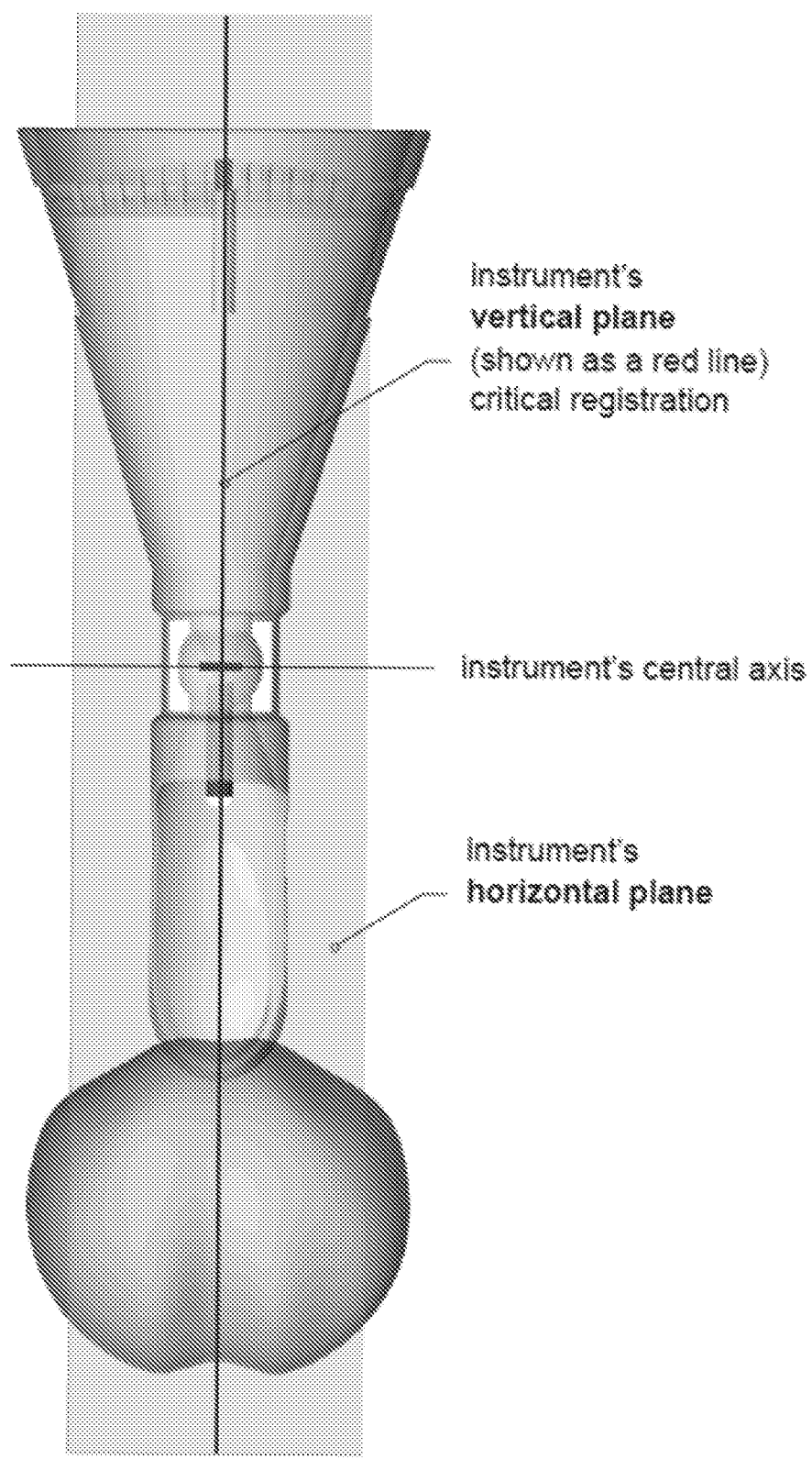
FIG. 14 is a top down view schematic showing the orientation of the needle guide, spherical targeting ball, and center bushing relative to the prostate used to define the vertical plane of an anatomical sensing system-guided prostate procedure device, in accordance with various embodiments.
Figure 15:
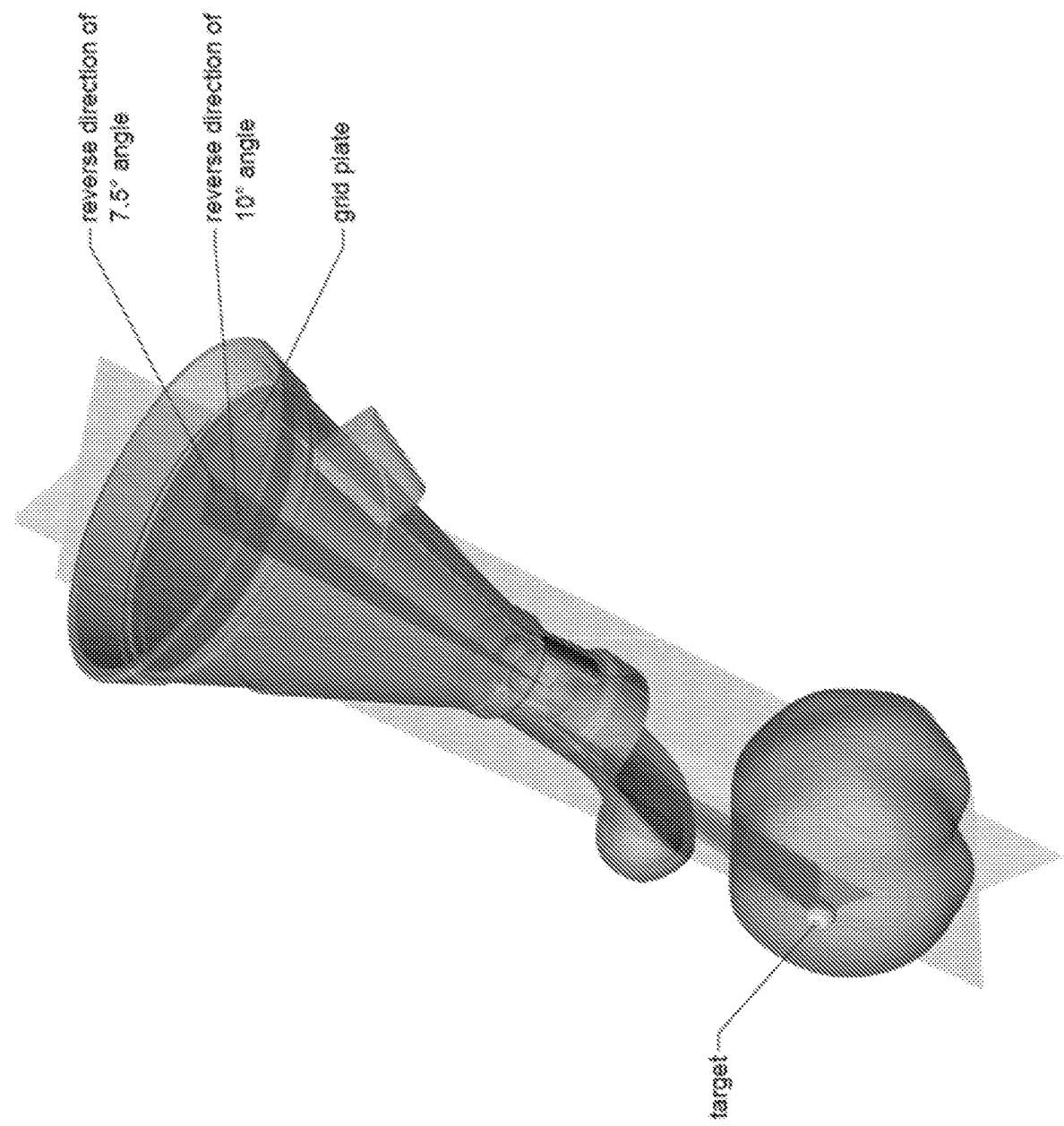
FIG. 15 is a perspective view schematic showing the angles of a suspicious section of prostate relative to the vertical plane and horizontal plane of an anatomical sensing system-guided prostate procedure device, in accordance with various embodiments.

As shown in the FIG. 13, MRI data is obtained and viewed perpendicular to the sagittal plane to identify and locate the anatomical sensing system-guided prostate procedure device's three principal targets. The three principal targets are the needle guide tip, the spherical targeting ball, and the grid plate center bushing. This identifies the anatomical sensing system-guided prostate procedure device's horizontal plane. As depicted in FIG. 14, MRI data is obtained and viewed perpendicular to instrument's horizontal plane to identify and locate the anatomical sensing system-guided prostate procedure device's three principal targets. Again, the three principal targets are the needle guide tip, the spherical targeting ball, and the grid plate center bushing. This identifies the anatomical sensing system-guided prostate procedure device's vertical plane. MRI data is collected and viewed parallel to instrument's vertical plane. MRI image slices are stepped through to locate suspicious areas of the prostate for biopsy analysis. The position of these areas are locked and the angle between center of target and central axis of instrument is the measured and/or recorded. An angle of 10° is determined between the target and the horizontal plane. MRI data is collected and viewed parallel to instrument's horizontal plane. MRI image slices are stepped through to locate and suspicious areas of the prostate for biopsy analysis. The position of these areas are locked and the angle between center of target and central axis of instrument is the measured and/or recorded. An angle of 7.5° is determined between the target and the vertical plane. As depicted in FIG. 15 the angles derived as above are translated through the central axis of the instrument to the grid plate. As depicted in FIG. 16, the angle relative to the origin is located on the back of the grid plate. In the embodiment shown, the angular distance between each guide hole is 2.5°. Each angle on the horizontal plane defines movement from side to side. Each angle on the vertical plane defines movement up and down. Thus as shown in the diagram, the needle target is three holes to the right and four holes down from the center origin. In the embodiment shown when capturing an angle, the value is rounded up or down to the closest 2.5° increment. For example, if the captured reading is 8°, round down to 7.5°. If the reading is 19°, round up to 20°.

Figure 17:
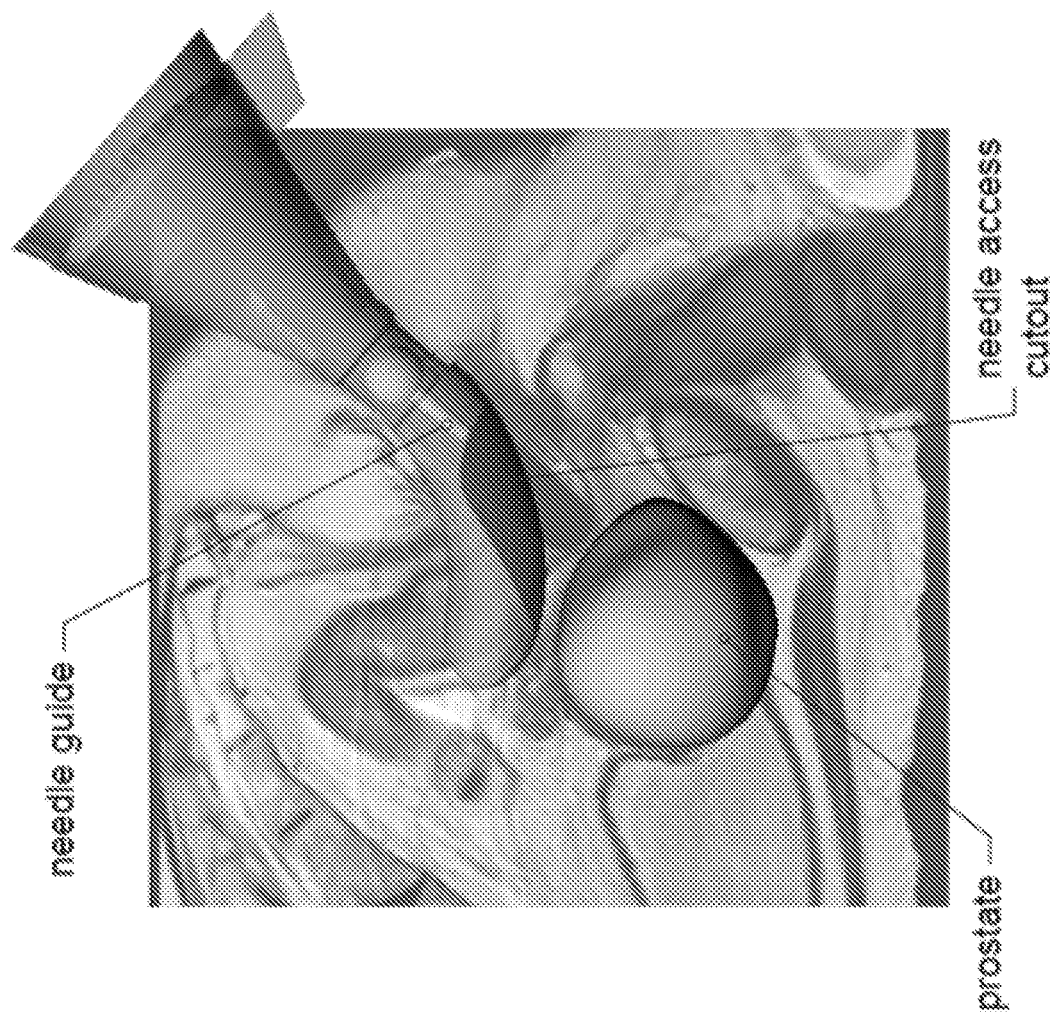
FIG. 17 is a schematic side view of an anatomical sensing system-guided prostate procedure device superimposed on an image of the prostate and bowel of a subject, in accordance with various embodiments.

FIG. 17 is a schematic side view of an anatomical sensing system-guided prostate procedure device superimposed on an image of the prostate and bowel of a subject. As shown, the device, when inserted, is situated a short distance from the prostate. Removing the needle access cutout illustrates that the probe is as close to the prostate as the anatomy allows.

Figure 18:
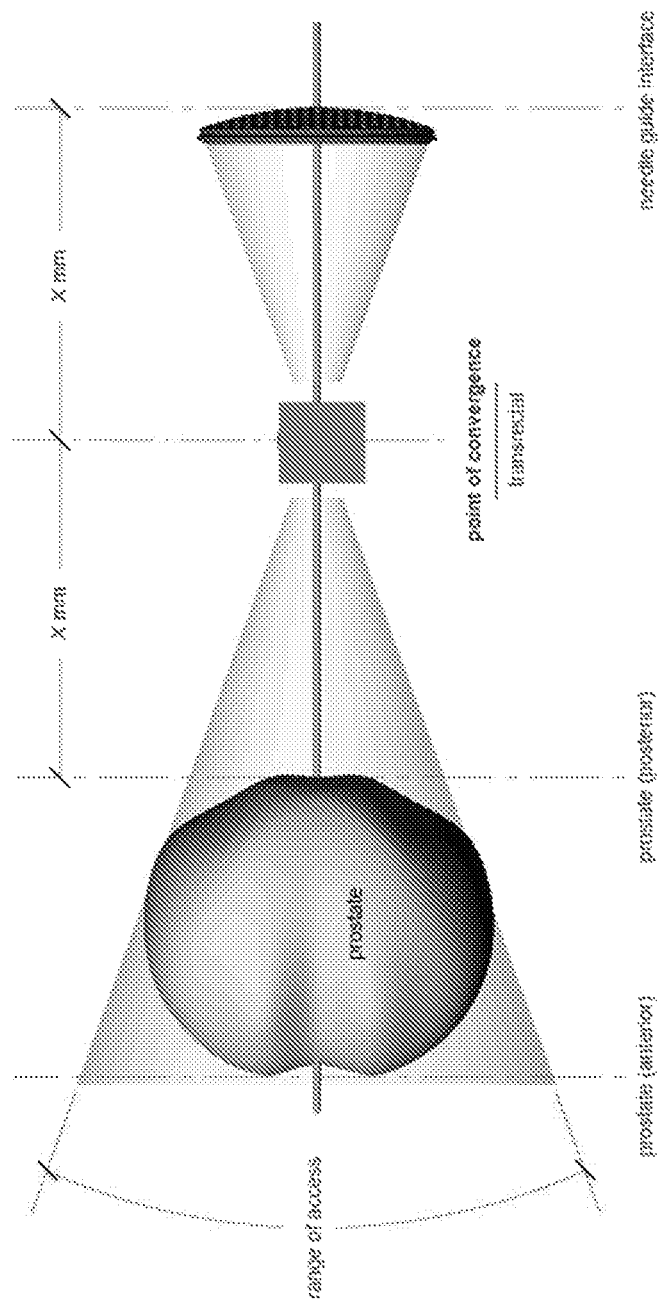
FIG. 18 is a schematic top down view of the correspondence between the zone of prostate access and biopsy needle range of motion, in accordance with various embodiments.

FIG. 18 is a schematic top down view of the correspondence between the zone of prostate access and the intersection of the proximal and distal cones showing instrument range of motion, in accordance with various embodiments. As is shown in FIG. 18, the proximal and distal cones intersect at the convergence point, which is shown as a black box.

Figure 19:
FIG. 19 is a schematic side view of an anatomical sensing system-guided prostate procedure device superimposed on an image of the prostate and bowel of a subject, in accordance with various embodiments.

FIG. 19 is a schematic side view of the sections of the anatomical sensing system-guided prostate procedure device superimposed on an image of the prostate and bowel of a subject, in accordance with various embodiments. As shown in this view, anatomical sensing system detectable markers can be used to determine the location of the components of the system relative to the anatomical features of a subject, such as the prostate of the subject.

Figure 20:
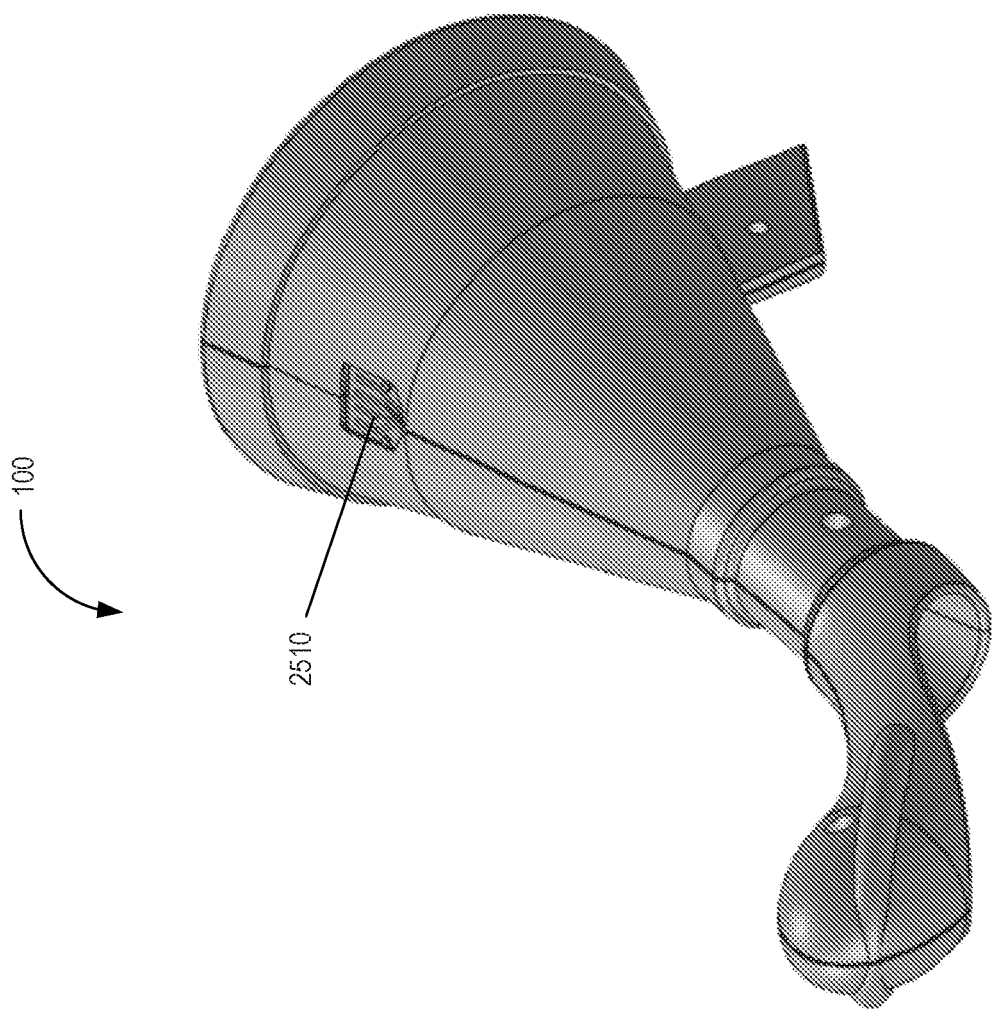
FIG. 20 is a perspective view of an anatomical sensing system-guided prostate procedure device showing the connections for an imaging coil, in accordance with various embodiments.

FIG. 20 is a perspective of an anatomical sensing system-guided prostate procedure device shown in showing the power supply coupling for an imaging coil, in accordance with various embodiments.

Figure 21:
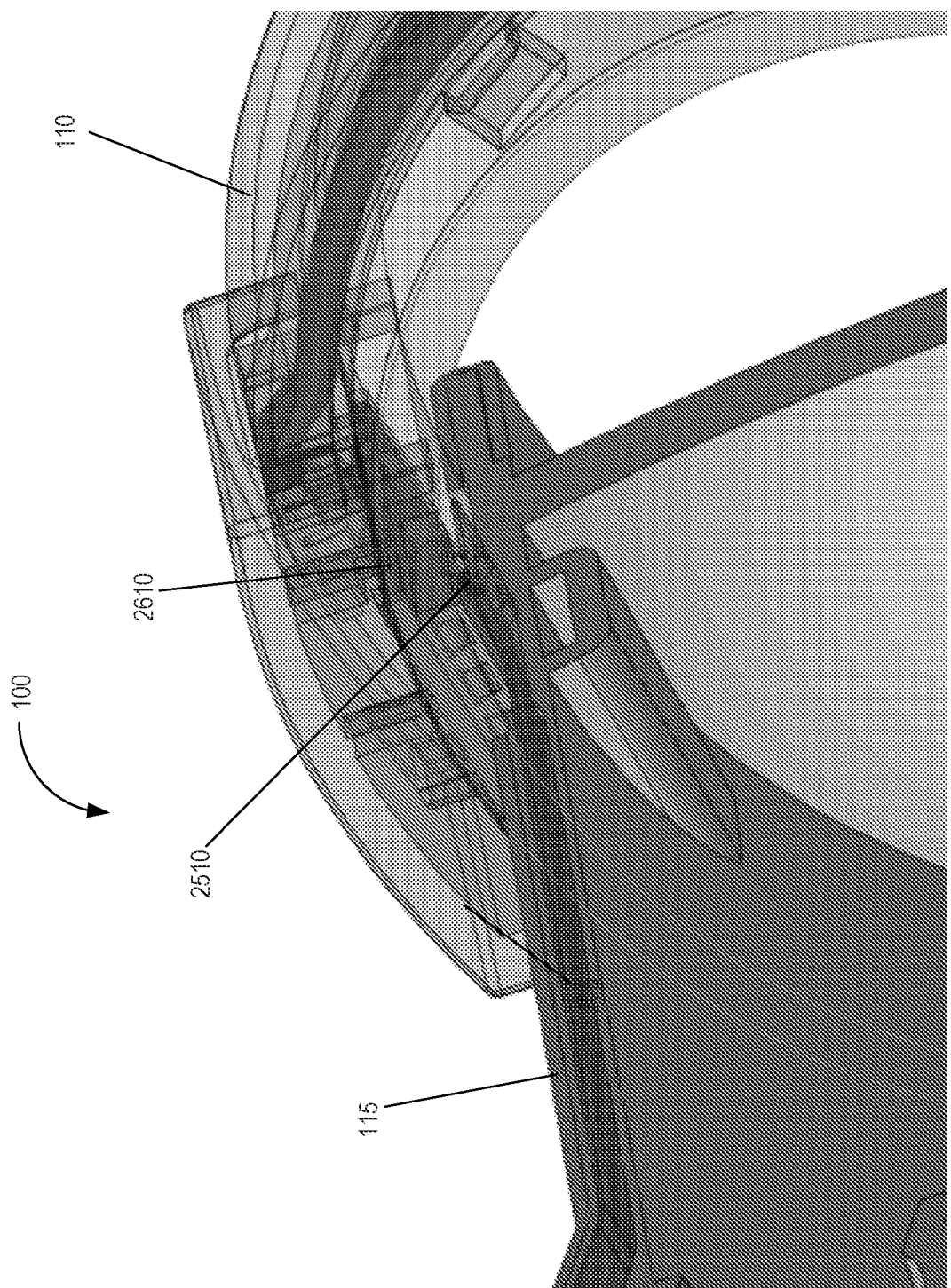
FIG. 21 is a close up of showing the connections between an interface board and an imaging coil, in accordance with various embodiments.

FIG. 21 is a close up of showing the power supply coupling for an imaging coil, in accordance with various embodiments.

Figure 22:
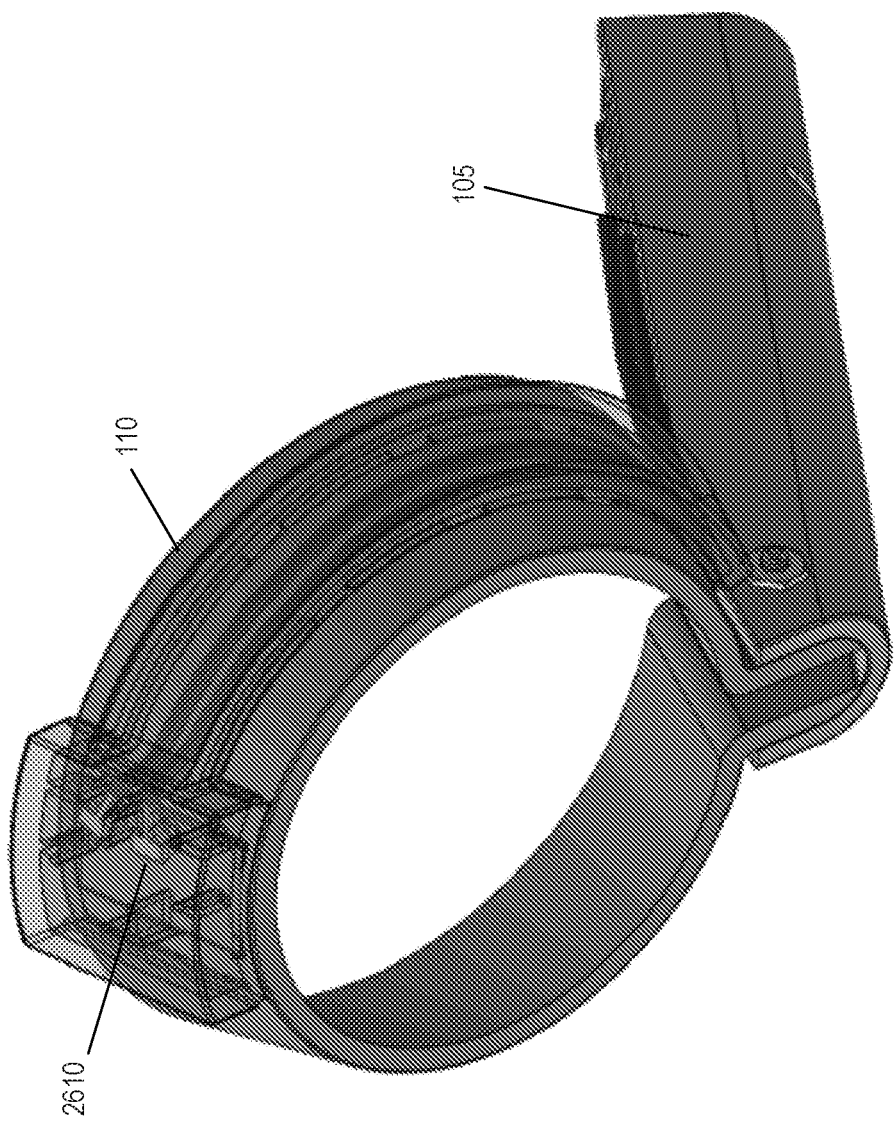
FIG. 22 is a perspective view of a clamp ring for an anatomical sensing system-guided prostate procedure device showing the connections between an interface board and external cables, in accordance with various embodiments.

FIG. 22 is a perspective of a clamp ring for an anatomical sensing system-guided prostate procedure device shown in showing the power supply coupling for an imaging coil, in accordance with various embodiments.

Figure 23:
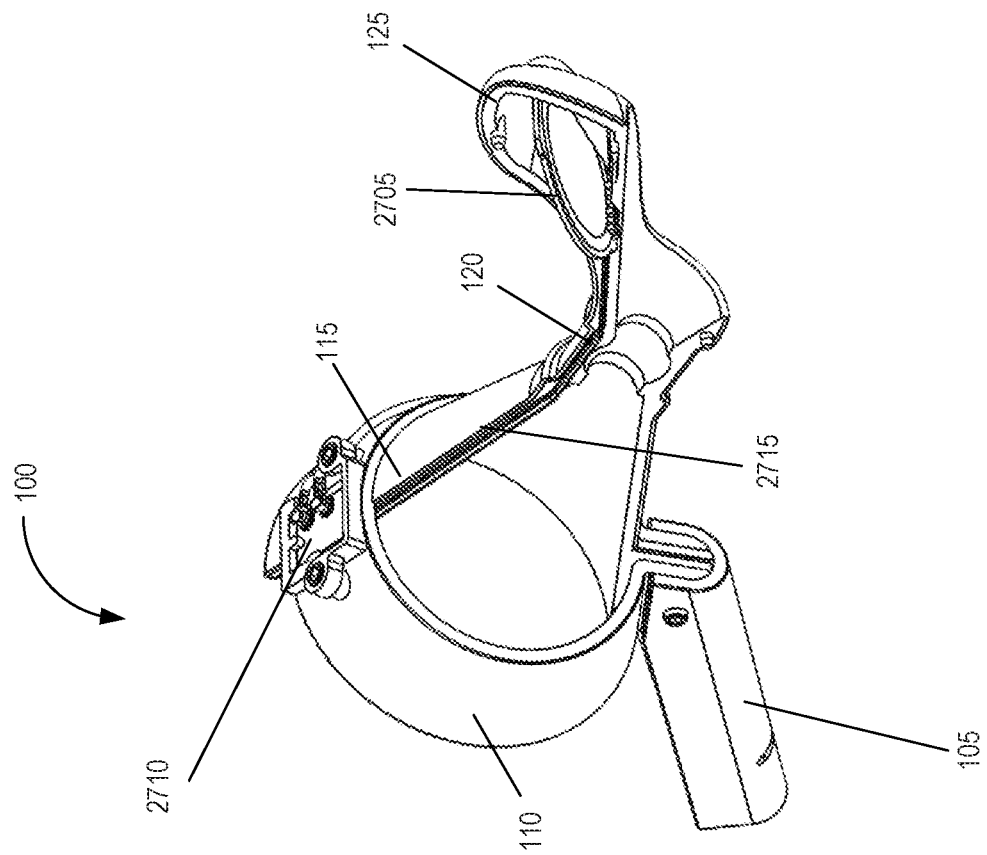
FIG. 23 is a perspective view of an anatomical sensing system-guided prostate procedure device showing a flexible circuit and an imaging coil, in accordance with various embodiments.

FIG. 23 is a perspective view of an anatomical sensing system-guided prostate procedure device 100 showing a flex circuit 2715 and an imaging coil 2705, in accordance with various embodiments. The device 100 includes the proximal housing section 115, the mid housing section 120, and the distal housing section 125. A compression sleeve 110 is fitted around the outer surface of the proximal housing section 115 and coupled to a clamp handle 105 on the inferior aspect of the device 100. The compression sleeve 110 may house connections and/or electronics (see FIGS. 24-26) and mates with connections on the outside surface of the device 100. The clamp handle 105 may be used fix the device 100 in a stationary position, for example, by clamping the clamp handle 105 to a table-mounted clamp stand (not shown). The flexible circuit 2715 runs proximally from the imaging coil 2705 from the distal housing section 125 through the mid housing section 120 to the proximal housing section 115, where it couples to the interface board. The materials of the flexible circuit 2715 are selected such that they are thin enough to pass through the construction at the mid housing section 120. In embodiments, the flexible circuit 2715 comprises thin metal strips on a polymer substrate. In certain embodiments, the metal comprises copper and the substrate comprises polyimide.

Figure 24:
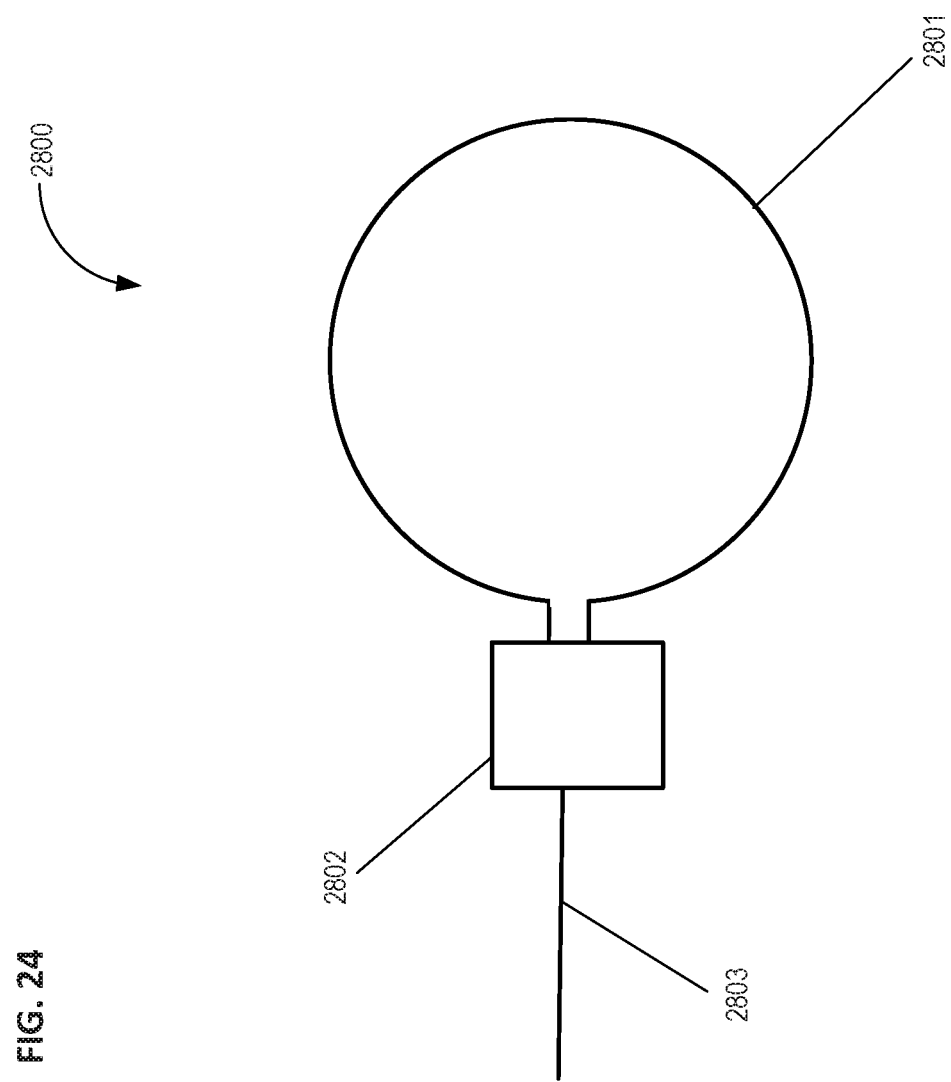
FIG. 24 is a schematic of an imaging coil, in accordance with various embodiments.

FIG. 24 is a schematic of an imaging coil, in accordance with various embodiments. As shown in FIG. 24, the imaging coil 2800 includes a loop antenna 2801, matching components 2802 and a signal wire 2803. The loop antenna 2801 creates a magnetic field that is primarily in the y-axis, where the BO field (magnetic field) is assumed to be approximately parallel to the z-axis and the length of the human body, and the y-axis is the vertical axis and the x-axis is the horizontal axis perpendicular to the human body. The antenna is assumed to be approximately in the x-z plane where inserted into the rectum of a subject.

Figure 25:
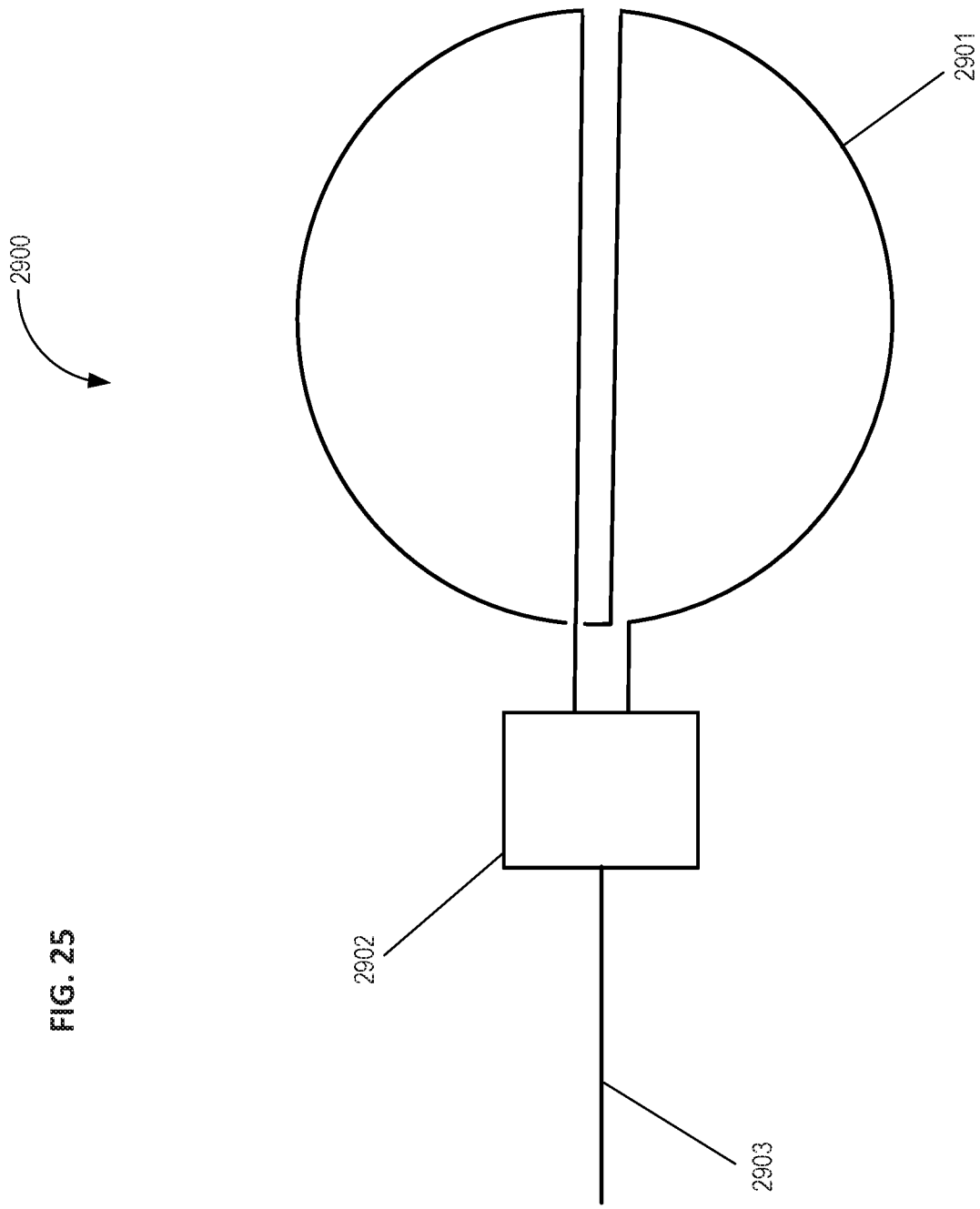
FIG. 25 is a schematic of an imaging coil, in accordance with various embodiments.

FIG. 25 is a schematic of an imaging coil, in accordance with various embodiments. As shown in FIG. 25, the imaging coil 2900 includes a butterfly antenna 2901, matching components 2902 and a signal wire 2903. The butterfly antenna 2901 creates a magnetic field that is primarily in the x-axis, where the BO field (magnetic field) is assumed to be approximately parallel to the z-axis and the length of the human body, and the y-axis is the vertical axis and the x-axis is the horizontal axis perpendicular to the human body. The antenna is assumed to be approximately in the x-z plane where inserted into the rectum of a subject.

Figure 26:
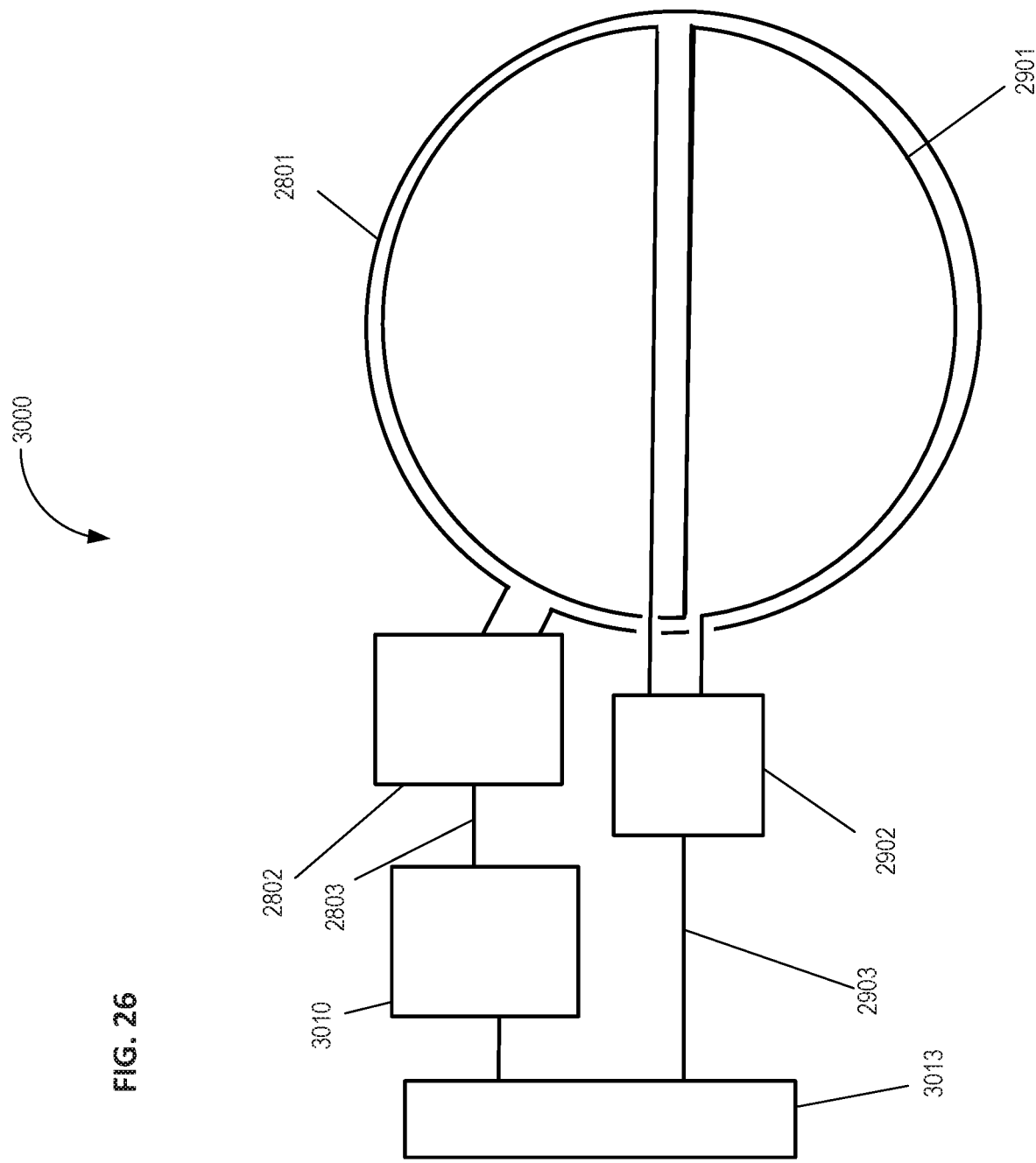
FIG. 26 is a schematic of the imaging coils of FIGS. 24 and 25 coupled together with selected electronics, in accordance with various embodiments.

FIG. 26 is a schematic of circularly polarized imaging composite coil 3000 made from the imaging coils of FIGS. 24 and 25 coupled together with selected electronics, in accordance with various embodiments. As shown in FIG. 26, the loop antenna 2801, matching components 2802 and a signal wire 2803 are interspaced with the butterfly antenna 2901, matching components 2902 and a signal wire 2903. The loop antenna 2801 creates a magnetic field that is primarily in the y-axis, where the BO field (magnetic field) is assumed to be approximately parallel to the z-axis and the length of the human body, and the y-axis is the vertical axis and the x-axis is the horizontal axis perpendicular to the human body. The butterfly antenna 2901 creates a magnetic field that is primarily in the x-axis. These dual antennas are driven with out of phase by 90 degrees with phase shifter 3010 to create a circularly polarized magnetic field. Using a coil in this configuration results in an approximately square root of 2 increase in signal-to-noise over a single antenna design. The imaging composite coil 3000 further includes a power splitter/combiner 3013 to manage the power and combine the signal from the loop antenna 2801 and the butterfly antenna 2901. The antenna is assumed to be approximately in the x-z plane where inserted into the rectum of a subject.

Figure 27:
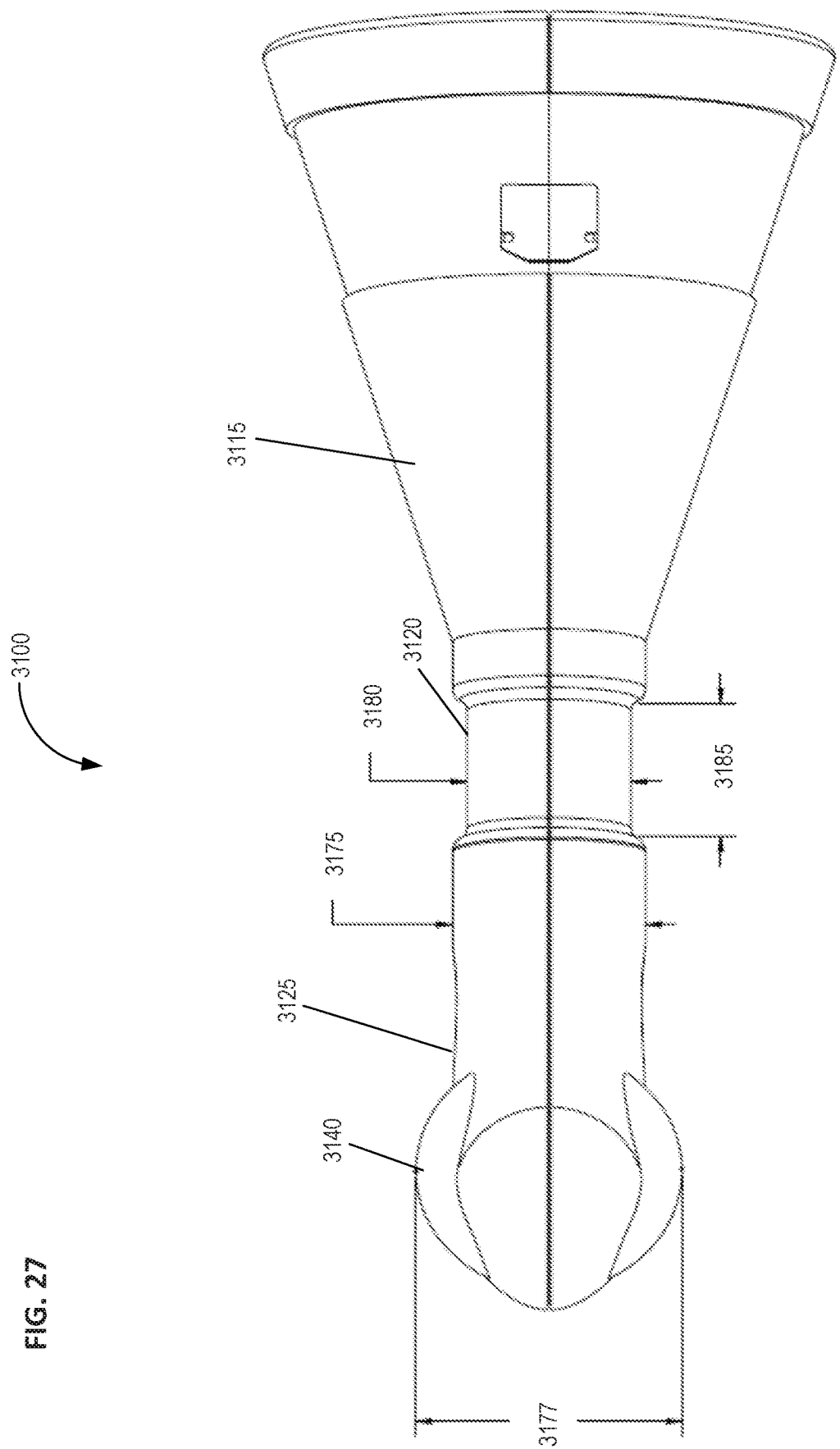
FIG. 27 is a cross sectional side view of an anatomical sensing system-guided prostate procedure device, in accordance with various embodiments.
Figure 28:
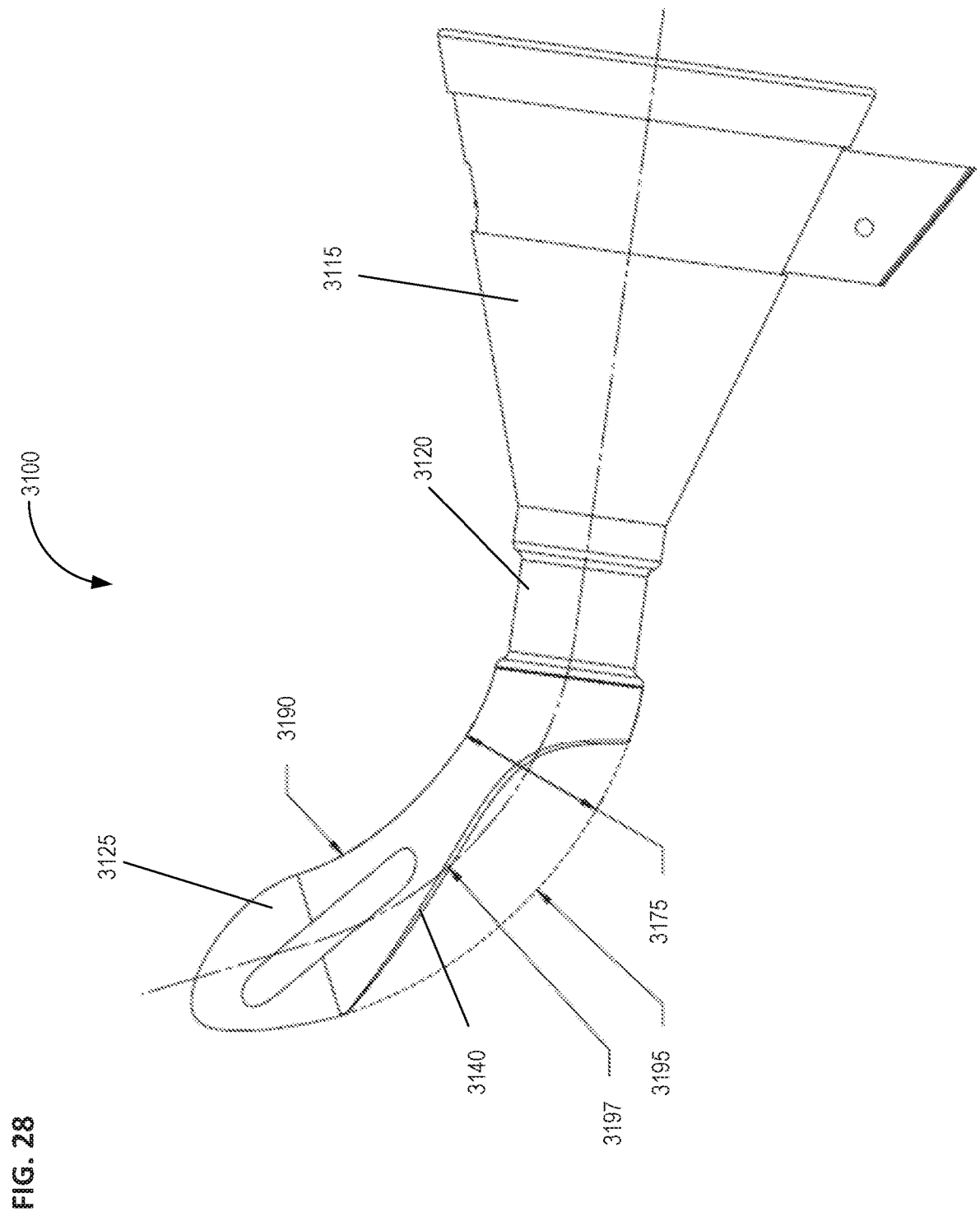
FIG. 28 a cross sectional side view of an anatomical sensing system-guided prostate procedure device, in accordance with various embodiments.

FIGS. 27 and 28 detail aspects of the mid and distal housing sections, in accordance with certain embodiments. FIG. 27 is a cross sectional side view of an anatomical sensing system-guided prostate procedure device, in accordance with various embodiments. FIG. 28 a cross sectional side view of an anatomical sensing system-guided prostate procedure device, in accordance with various embodiments. As shown in FIG. 27, the device 3100 includes a proximal housing section 3115, a mid housing section 3120, and a distal housing section 3125. The proximal housing section 3115 and mid housing section 120 are centered along a common longitudinal axis. The distal housing section 3125 section is angled superiorly away from this axis for example between about 10 to about 60 degrees away from the common longitudinal axis. The distal housing section 3125 may include a sub housing 3140 that is configured to contain an MRI imaging coil. The distal housing section 3125 has a width 3175, that is about 0.5 inches to about 1.5 inches. The sub housing has a width 3177 that is slightly larger than this. The mid housing section 3120 is recessed from both the distal housing section 3125 and the proximal housing section 3115 and configured to be retained in the anus of a subject, for example such that the anal orifice collapses around the recessed waist 3120 and helps to hold and/or retain the device in place. The mid housing section 3120 has a diameter 3180 that is about 0.25 inches to about 1.0 inches in length. The mid housing section 3120 has a length 3185 that is about 0.25 inches to about 1.0 inches in length.

As shown in FIG. 28, the device 3100 includes a proximal housing section 3115, a mid housing section 3120, and a distal housing section 3125. The proximal housing section 3115 and mid housing section 120 are centered along a common longitudinal axis. The distal housing section 3125 section is angled superiorly away from this axis for example between about 10 to about 60 degrees away from the common longitudinal axis. The distal housing section 3125 has a width 3175, that is about 0.5 inches to about 1.5 inches. The mid housing section 3120 is recessed from both the distal housing section 3125 and the proximal housing section 3115 and configured to be retained in the anus of a subject, for example such that the anal orifice collapses around the recessed waist 3120 and helps to hold and/or retain the device in place. The distal housing section has an internal radius 3195, an external radius, and a centerline radius 3197. The centerline radius 3197 is about 1.75 inches to about 2.25 inches. The internal radius 3190 is about 1.5 inches to about 1.9 inches. The external radius 3195 is about 2.25 inches to about 2.75 inches. Also shown in this view is the cut out 3140.

FIG. 29 is a schematic of an exemplary matching circuit 2802 to be used between an input signal wire 2803 (depicted here as part of a grounded coaxial cable 2810) and a loop antenna 2801, in accordance with various embodiments. The matching network pictured here uses 3 capacitors 2811, 2812, 2813 to match the impedance of the driving signal to the impedance of the antenna 2801 in order maximize the power transfer. In embodiments, matching circuit components may be specified to impart a signal impedance of about 50 ohms. It will be recognized by those with skill in the electrical arts that other topologies and components can be used to match the signal input to the antenna. For example, inductors and or resistors can be used to construct a suitable matching circuit.

FIG. 30 is a schematic of an exemplary 90 degree phase shift circuit, as might be used for the phase shifter component 3010 in accordance with various embodiments. The signal input at node A 3020 is shifted by 90 degrees and appears at output node B 3030. The phase shifter circuit pictured here uses 2 inductors 3021, 3022 and three capacitors 3023, 3024, 3025. It will be recognized by those with skill in the electrical arts that other topologies and components can be used to construct a phase shifter circuit for use in the disclosed system. Further, the components of the 90 degree phase shifter maybe selected to impart a specific frequency of operation. In embodiments, phase shifter circuit components may be specified to impart a signal impedance of about 50 ohms.

FIG. 31 is a schematic of an exemplary power splitter combiner circuit, in accordance with various embodiments. As a RF power splitter the input signal is attached at node C 3050 and half of the power appears at node D 3060 and the other half at node E 3070. As a power combiner the in phase signals that are on node D 3060 and node E 3070 are combined and are output on node C 3050. In the circuit depicted here, three capacitors 3051, 3052, 3053, two inductors 3055, 3056, and one resistor 3058 are used to create a power splitter combiner. It will be recognized by those with skill in the electrical arts that other topologies and components can be used to construct a power slitter combiner for use in the disclosed system. In embodiments, the components of power splitter combiner circuit may be specified to impart a signal impedance of about 50 ohms.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. An anatomical sensing system-guided prostate procedure device, comprising:
   a housing having a proximal end, a distal end, a proximal housing section, and a distal housing section, wherein the distal housing section is configured for insertion into an anus and retention in a rectum of a subject;
   an instrument convergence point disposed between the proximal end and the distal end, the instrument convergence point defined by an intersection of a proximal cone and a distal cone defining the range of motion of an instrument both proximal and distal to the instrument convergence point, and configured to allow the instrument to pass through the instrument convergence point at a variable and selectable angle; and
   an instrument angle orienting system at the proximal end of the housing, the instrument angle orienting system directing an orientation of the variable angle in three-dimensions about the instrument convergence point, wherein the instrument angle orienting system comprises a fixed array instrument angle orienting system, and wherein the fixed array instrument angle orienting system comprises a grid array plate disposed within the proximal housing section, the grid array plate having a plurality of instrument access channels each with a channel axis and oriented such that each channel axis converges to the instrument convergence point.

2. The anatomical sensing system-guided prostate procedure device of claim 1, wherein the instrument convergence point is contained within a mechanism configured to direct the instrument to three-dimensional locations distally.

3. The anatomical sensing system-guided prostate procedure device claim 1, wherein the instrument angle orienting system directs one or more of a penetration depth of a distal end of the instrument and a location in three-dimensions of a distal tip of the instrument.

4. The anatomical sensing system-guided prostate procedure device of claim 1, further comprising an instrument guide.

5. The anatomical sensing system-guided prostate procedure device of claim 4, wherein the instrument guide is conical.

6. The anatomical sensing system-guided prostate procedure device of claim 1, wherein the instrument convergence point is translatable along an axis running from the proximal end of the housing and the distal end of the housing.

7. The anatomical sensing system-guided prostate procedure device of claim 1, wherein the housing comprises a mid housing section and wherein the anatomical sensing system-guided prostate procedure device further comprises a spherical targeting ball rotationally constrained within the mid housing section and centered about the instrument convergence point.

8. The anatomical sensing system-guided prostate procedure device of claim 1, wherein the anatomical sensing system-guided prostate procedure device comprises a Magnetic Resonance, Computed Tomography (CT) or an Ultrasound-anatomical sensing system.

9. The anatomical sensing system-guided prostate procedure device of claim 1, further comprising a biopsy needle, a probe, sensor system, surgical device, therapeutic instrument system, or an agent placement device.

10. The anatomical sensing system-guided prostate procedure device of claim 1, further comprising at least one MRI coil.

11. The anatomical sensing system-guided prostate procedure device of claim 10, wherein the housing comprises a mid housing section, and wherein the at least one MRI coil is disposed within the distal housing section on an interior surface of the proximal end of the housing or traverses the distal housing section and the mid housing section.

12. The anatomical sensing system-guided prostate procedure device of claim 10, wherein the at least one MRI coil comprises a loop antenna, a butterfly antenna, or a combination thereof.

13. The anatomical sensing system-guided prostate procedure device of claim 10, wherein the housing comprises a mid housing section, the anatomical sensing system-guided prostate procedure device further comprising a flexible circuit running from the MRI coil through the mid housing section to the proximal housing section and an interface board coupled to a proximal end of the flexible circuit.

14. The anatomical sensing system-guided prostate procedure device of claim 1 further comprising a clamp handle coupled to the proximal housing section.

15. The anatomical sensing system-guided prostate procedure device of claim 1, further comprising one or more points of an anatomical sensing system detectable agent for locating the device.

16. The anatomical sensing system-guided prostate procedure device of claim 1, wherein the distal housing section includes a cut out that allows an instrument to pass through the device.

17. The anatomical sensing system-guided prostate procedure device of claim 1, wherein the distal housing section is configured to conform to a human rectum.

18. The anatomical sensing system-guided prostate procedure device of claim 1 wherein the distal housing section is angled superiorly about 10 to about 60 degrees away from a centerline of the housing.

19. A system, comprising the device of claim 1 and an instrument for conducting a medical procedure.

20. A method of performing an anatomical sensing system-guided procedure on a subject's prostate, comprising:
    introducing a distal end of the anatomical sensing system-guided prostate procedure device of claim 1 into a rectum of a subject in proximity to a prostate of the subject;
    obtaining data on anatomical features of the subject, including the prostate, and the anatomical sensing system-guided prostate procedure device using an anatomical sensing system;
    establishing a position of the device and the prostate;
    determining the location in three-dimensional space of tissue on or within the prostate for the procedure;
    translating the location in three-dimensional space to the instrument angle orienting system; and
    using the instrument angle orienting system to guide the instrument to the prostate, thereby performing the procedure.

21. An anatomical sensing system-guided prostate procedure device, comprising:
    a housing having a proximal end, a distal end, a proximal housing section, and a distal housing section, wherein the distal housing section is configured for insertion into an anus and retention in a rectum of a subject;
    an instrument convergence point disposed between the proximal end and the distal end, the instrument convergence point defined by an intersection of a proximal cone and a distal cone defining the range of motion of an instrument both proximal and distal to the instrument convergence point, and configured to allow the instrument to pass through the instrument convergence point at a variable and selectable angle; and
    an instrument angle orienting system at the proximal end of the housing, the instrument angle orienting system directing an orientation of the variable angle in three-dimensions about the instrument convergence point, wherein the instrument angle orienting system comprises a continuously variable coordinate instrument angle orienting system, wherein the continuously variable coordinate instrument angle orienting system comprises a Cartesian coordinate or a conical coordinate instrument angle orienting system, wherein the continuously variable coordinate instrument angle orienting system comprises a circular plate rotationally disposed within the proximal housing section, and wherein the circular plate has a center and comprises a cutout guide extending radially from the center of the circular plate and an indexing carriage slidably disposed within the cutout guide, and wherein an instrument guide extends proximally from the instrument convergence point to the indexing carriage.

* * * * *